United States Patent
Lee et al.

(10) Patent No.: US 12,258,504 B2
(45) Date of Patent: Mar. 25, 2025

(54) METHOD FOR MANUFACTURING A LIGHT EMITTING ELEMENT INCLUDING A QUANTUM DOT COMPOSITION

(71) Applicant: SAMSUNG DISPLAY CO., LTD., Yongin-si (KR)

(72) Inventors: Changhee Lee, Seoul (KR); Dukki Kim, Suwon-si (KR); Hyojin Ko, Seoul (KR); Sehun Kim, Yongin-si (KR); Jaehoon Kim, Seoul (KR); Hyunmi Doh, Seoul (KR); Yunku Jung, Cheonan-si (KR); Jaekook Ha, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 18/407,326

(22) Filed: Jan. 8, 2024

(65) Prior Publication Data

US 2024/0141228 A1    May 2, 2024

Related U.S. Application Data

(62) Division of application No. 17/192,388, filed on Mar. 4, 2021, now Pat. No. 11,866,627.

(30) Foreign Application Priority Data

Jun. 2, 2020 (KR) .......................... 10-2020-0066596

(51) Int. Cl.
*C09K 11/06* (2006.01)
*C07C 43/10* (2006.01)
(Continued)

(52) U.S. Cl.
CPC .............. *C09K 11/06* (2013.01); *C07C 43/10* (2013.01); *C07C 53/00* (2013.01); *C07C 63/08* (2013.01); *C07C 211/09* (2013.01); *C07C 309/04* (2013.01); *C07C 309/30* (2013.01); *C07F 9/5407* (2013.01); *C07F 9/5442* (2013.01); *H10K 85/60* (2023.02); *C09K 2211/10* (2013.01); *C09K 2211/1007* (2013.01); *H10K 50/115* (2023.02); *H10K 71/00* (2023.02); *H10K 71/15* (2023.02)

(58) Field of Classification Search
CPC ............... C09K 11/06; C09K 2211/10; C09K 2211/1007; C09K 11/025; C09K 11/02;
(Continued)

(56) References Cited

U.S. PATENT DOCUMENTS 6,310,189 B1 * 10/2001 Fodor .................... C07C 229/14
                                                                            536/25.31
6,506,558 B1 *  1/2003 Fodor ................ G11C 13/0019
                                                                            506/16

(Continued)

FOREIGN PATENT DOCUMENTS

CN          108913142 A      11/2018
CN          109468134 A       3/2019
(Continued)

OTHER PUBLICATIONS

Carey, Graham H. et al., "Cleavable Ligands Enable Uniform Close Packing in Colloidal Quantum Dot Solids", *ACS Applied Materials & Interfaces*, Sep. 17, 2015, vol. 7, p. 21995-22000.
(Continued)

*Primary Examiner* — Caleb E Henry
(74) *Attorney, Agent, or Firm* — Womble Bond Dickinson (US) LLP

(57) ABSTRACT

A quantum dot composition includes a quantum dot, and a ligand bonded to a surface of the quantum dot, wherein the ligand includes a head portion bonded to the surface of the quantum dot and containing a polar solvent dissociative functional group, and a tail portion connected to the head portion. A quantum dot composition according to an embodiment is used to form an emission layer of a light emitting element to enhance luminous efficiency of the light emitting element including an emission layer formed through the quantum dot composition.

5 Claims, 10 Drawing Sheets

(51) Int. Cl.
| | |
|---|---|
| *C07C 53/00* | (2006.01) |
| *C07C 63/08* | (2006.01) |
| *C07C 211/09* | (2006.01) |
| *C07C 309/04* | (2006.01) |
| *C07C 309/30* | (2006.01) |
| *C07F 9/54* | (2006.01) |
| *H10K 50/115* | (2023.01) |
| *H10K 71/00* | (2023.01) |
| *H10K 71/15* | (2023.01) |
| *H10K 85/60* | (2023.01) |

(58) Field of Classification Search
CPC ..... C09K 2211/18; C07C 43/10; C07C 53/00; C07C 63/08; C07C 211/09; C07C 309/04; C07C 309/30; C07F 9/5407; C07F 9/5442; C07F 9/094; H10K 85/60; H10K 50/115; H10K 71/00; H10K 71/15; H10K 71/441; H10K 85/30; H10K 71/12
See application file for complete search history.

(56) References Cited

U.S. PATENT DOCUMENTS

| | | | | |
|---|---|---|---|---|
| 7,294,449 | B1* | 11/2007 | Gudeman | G03F 7/0047 430/270.1 |
| 7,595,118 | B2* | 9/2009 | Chun | B82Y 10/00 428/917 |
| 7,863,812 | B2* | 1/2011 | Hung | H10K 50/11 313/506 |
| 8,343,627 | B2* | 1/2013 | Zhong | G01N 33/54326 428/403 |
| 8,597,730 | B2 | 12/2013 | Pickett et al. | |
| 9,492,840 | B2 | 11/2016 | Lee et al. | |
| 9,554,484 | B2 | 1/2017 | Rogers et al. | |
| 9,559,322 | B2* | 1/2017 | Ko | C09K 11/565 |
| 9,691,873 | B2 | 6/2017 | Rogers et al. | |
| 9,723,122 | B2 | 8/2017 | Ghaffari et al. | |
| 9,765,934 | B2 | 9/2017 | Rogers et al. | |
| 9,770,349 | B2 | 9/2017 | Owens et al. | |
| 9,793,505 | B2 | 10/2017 | Zhou et al. | |
| 9,812,004 | B1* | 11/2017 | Boshernitzan | G08C 17/02 |
| 9,831,706 | B2* | 11/2017 | MacWilliams | H02J 7/32 |
| 9,874,693 | B2* | 1/2018 | Baiocco | H01L 21/762 |
| 9,936,574 | B2 | 4/2018 | Rogers et al. | |
| 9,943,840 | B2* | 4/2018 | Shaffer | B01J 23/06 |
| 9,947,817 | B2 | 4/2018 | Smith et al. | |
| 9,954,126 | B2 | 4/2018 | Smith et al. | |
| 10,388,902 | B1* | 8/2019 | Palles-Dimmock | H10K 50/115 |
| 11,056,650 | B2 | 7/2021 | Kang et al. | |
| 11,591,515 | B2 | 2/2023 | Kim et al. | |
| 11,618,853 | B2 | 4/2023 | Peng et al. | |
| 2003/0042850 | A1 | 3/2003 | Bertram et al. | |
| 2004/0146560 | A1 | 7/2004 | Whiteford et al. | |
| 2006/0068154 | A1 | 3/2006 | Parce et al. | |
| 2007/0134699 | A1* | 6/2007 | Glover, III | B01J 19/0046 977/924 |
| 2010/0044635 | A1 | 2/2010 | Breen et al. | |
| 2010/0068522 | A1* | 3/2010 | Pickett | B82Y 30/00 977/773 |
| 2010/0113813 | A1* | 5/2010 | Pickett | C09C 3/08 977/774 |
| 2010/0213438 | A1* | 8/2010 | Cho | H10K 50/156 438/47 |
| 2011/0006269 | A1* | 1/2011 | Petruska | C01G 15/00 977/773 |
| 2011/0037029 | A1* | 2/2011 | Liu | C08G 65/3322 252/500 |
| 2011/0175064 | A1* | 7/2011 | Kim | H10K 59/805 438/22 |
| 2011/0294995 | A1* | 12/2011 | Huo | C08L 33/02 977/773 |
| 2012/0270231 | A1* | 10/2012 | Smith | C09K 11/02 435/7.1 |
| 2012/0280345 | A1* | 11/2012 | Zhu | G02B 6/1226 257/E31.127 |
| 2012/0319089 | A1* | 12/2012 | Shin | H10K 71/00 257/E51.024 |
| 2013/0004522 | A1* | 1/2013 | Dvir | A61K 9/5138 424/178.1 |
| 2013/0146854 | A1* | 6/2013 | Dong | H10K 50/12 438/45 |
| 2013/0345458 | A1* | 12/2013 | Freeman | C08G 77/38 556/439 |
| 2014/0027816 | A1* | 1/2014 | Cea | H01L 29/1054 257/E29.085 |
| 2014/0197507 | A1* | 7/2014 | Assefa | H01L 31/0745 438/69 |
| 2014/0302627 | A1* | 10/2014 | Ko | C09K 11/565 252/301.16 |
| 2015/0031217 | A1* | 1/2015 | Naasani | C09K 11/883 438/780 |
| 2015/0076469 | A1 | 3/2015 | Ikemizu et al. | |
| 2015/0091093 | A1* | 4/2015 | Bouche | H01L 29/45 257/369 |
| 2015/0267106 | A1* | 9/2015 | Pillay Narrainen | H01L 33/502 252/301.36 |
| 2015/0268417 | A1* | 9/2015 | Assefa | H01L 27/1461 385/14 |
| 2015/0287927 | A1 | 10/2015 | Okubo et al. | |
| 2017/0125707 | A1* | 5/2017 | Yamaguchi | C07F 15/0033 |
| 2017/0179409 | A1 | 6/2017 | Yamaguchi et al. | |
| 2017/0213989 | A1 | 7/2017 | Tsunoi et al. | |
| 2018/0033994 | A1* | 2/2018 | Jang | H10K 50/165 |
| 2018/0298154 | A1* | 10/2018 | Lundorf | C04B 35/48 |
| 2018/0366653 | A1 | 12/2018 | He et al. | |
| 2019/0086733 | A1 | 3/2019 | Min et al. | |
| 2019/0097101 | A1 | 3/2019 | Dorman | |
| 2019/0103524 | A1* | 4/2019 | Jang | G02F 1/133603 |
| 2019/0115492 | A1 | 4/2019 | Tamma et al. | |
| 2019/0115550 | A1 | 4/2019 | Kim et al. | |
| 2019/0198728 | A1 | 6/2019 | Tamma et al. | |
| 2019/0302615 | A1* | 10/2019 | Krysak | G03F 7/0043 |
| 2019/0348577 | A1 | 11/2019 | Pathak et al. | |
| 2020/0013967 | A1 | 1/2020 | Yamada et al. | |
| 2020/0119297 | A1 | 4/2020 | Lee et al. | |
| 2020/0131435 | A1* | 4/2020 | Pousthomis | B01J 19/06 |
| 2020/0135984 | A1* | 4/2020 | Jang | C09K 11/70 |
| 2020/0181157 | A1* | 6/2020 | Lee | H10K 85/636 |
| 2020/0270517 | A1 | 8/2020 | Bisri et al. | |
| 2020/0273926 | A1* | 8/2020 | Lee | H10K 71/00 |
| 2021/0043863 | A1* | 2/2021 | Jung | H10K 85/30 |
| 2021/0074939 | A1 | 3/2021 | Jung et al. | |
| 2021/0091324 | A1* | 3/2021 | Jung | H05B 33/14 |
| 2021/0179939 | A1* | 6/2021 | Stokes | C09K 11/565 |
| 2021/0371732 | A1 | 12/2021 | Lee et al. | |
| 2021/0371736 | A1 | 12/2021 | Lee et al. | |
| 2021/0371737 | A1 | 12/2021 | Jung et al. | |
| 2021/0371738 | A1 | 12/2021 | Lee et al. | |
| 2021/0371739 | A1 | 12/2021 | Lee et al. | |
| 2021/0376242 | A1 | 12/2021 | Lee et al. | |

FOREIGN PATENT DOCUMENTS

| | | |
|---|---|---|
| CN | 110551495 A | 12/2019 |
| CN | 112552898 A | 3/2021 |
| CN | 112552899 A | 3/2021 |
| CN | 113764476 A | 12/2021 |
| EP | 3798282 A1 | 3/2021 |
| JP | 2005-502176 A | 1/2005 |
| KR | 10-2014-0121346 A | 10/2014 |
| KR | 10-2015-0063929 A | 6/2015 |
| KR | 10-1700382 B1 | 1/2017 |
| KR | 10-2018-0085232 A | 7/2018 |
| KR | 10-2018-0105873 A | 10/2018 |
| KR | 10-2019-0000941 A | 1/2019 |
| KR | 10-2019-0042192 A | 4/2019 |
| KR | 10-2019-0063544 A | 6/2019 |
| KR | 10-2019-0117890 | 10/2019 |
| KR | 10-2021-0031027 A | 3/2021 |

(56) References Cited

FOREIGN PATENT DOCUMENTS

| KR | 10-2021-0036435 A | 4/2021 |
| KR | 10-2021-0149950 A | 12/2021 |
| KR | 10-2021-0149956 A | 12/2021 |
| KR | 10-2021-0149968 A | 12/2021 |
| KR | 10-2021-0149971 A | 12/2021 |
| KR | 10-2021-0149974 A | 12/2021 |
| KR | 10-2021-0149975 A | 12/2021 |

OTHER PUBLICATIONS

Kovalenko, Maksym V. et al., "Nanocrystal Superlattices with Thermally Degradable Hybrid Inorganic-Organic Capping Ligands", *Journal of the American Chemical Society*, Oct. 11, 2010, vol. 132, No. 43, p. 15124-15126.

Boles et al., "The surface science of nanocrystals," Nature Materials, vol. 15, 2016, 14 pages.

Chinese Office action for Application No. 202110464081.0, mailed Nov. 11, 2024, 5 pages.

Pu et al., "Electrochemically-stable ligands bridge the photoluminescence-electroluminescence gap of quantum dots," Nature Communications, 10 pages, Feb. 18, 2020.

\* cited by examiner

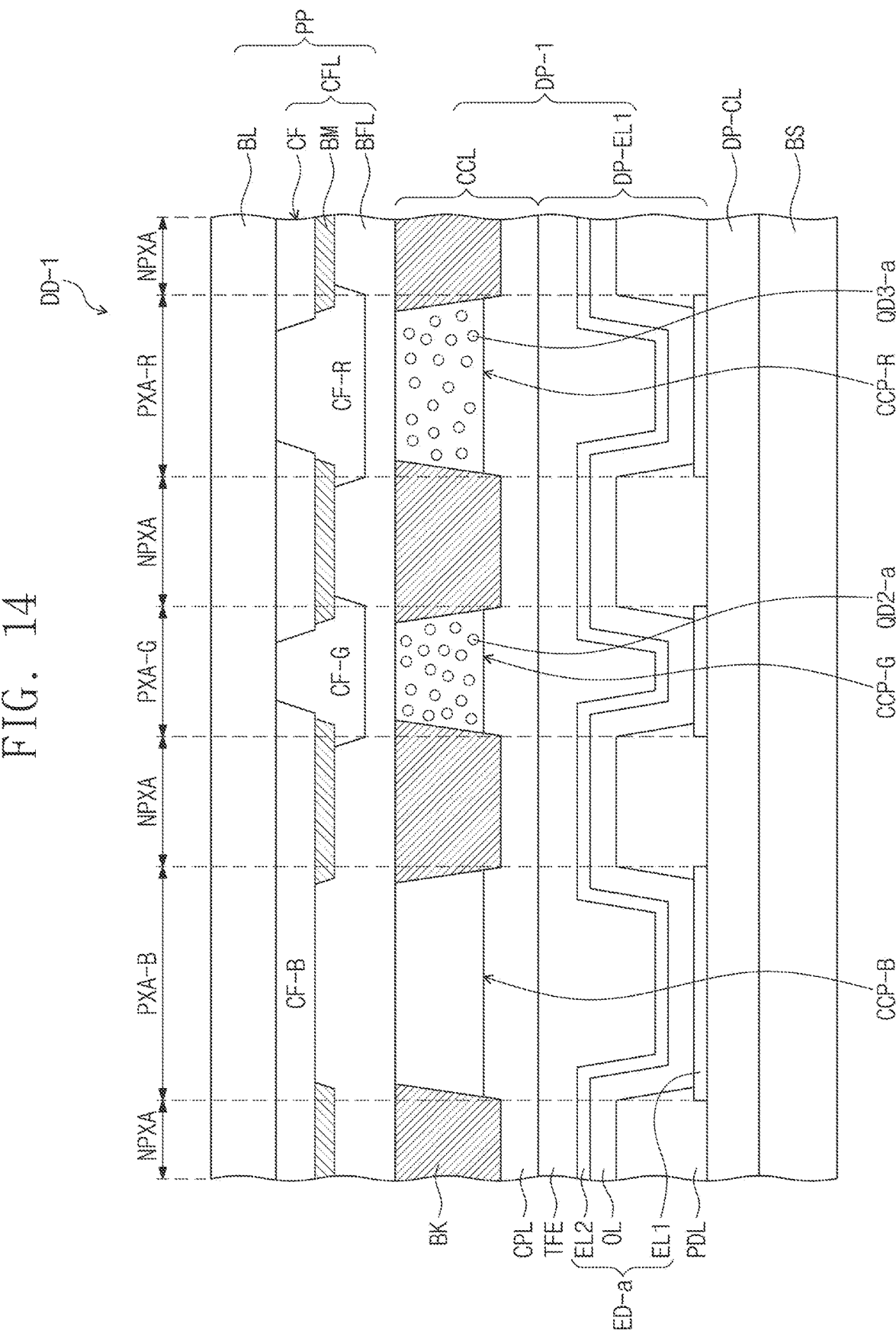

METHOD FOR MANUFACTURING A LIGHT EMITTING ELEMENT INCLUDING A QUANTUM DOT COMPOSITION

CROSS-REFERENCE TO RELATED APPLICATIONS

This application is a divisional of U.S. patent application Ser. No. 17/192,388, filed Mar. 4, 2021, which claims priority to and the benefit of Korean Patent Application No. 10-2020-0066596, filed Jun. 2, 2020, the entire content of both of which is incorporated herein by reference.

BACKGROUND

1. Field

One or more aspects of embodiments of the present disclosure relate to a quantum dot composition, a light emitting element including an emission layer formed from a quantum dot composition, and a method for manufacturing the same.

2. Description of the Related Art

Various types of display devices used in multimedia devices (such as a television set, a mobile phone, a tablet computer, a navigation system, and/or a game console) are being developed. In such display devices, a so-called self-luminescent display element is used, which accomplishes display by causing an organic compound-containing light emitting material to emit light.

In addition, light emitting elements using quantum dots as a light emitting material are being developed to enhance the color reproducibility of display devices, and there is a demand for increasing the luminous efficiency and service life of a light emitting element using quantum dots.

SUMMARY

One or more aspects of embodiments of the present disclosure are directed toward a quantum dot composition that can be used in an emission layer of a light emitting element to exhibit improved luminous efficiency.

One or more aspects of embodiments of the present disclosure are directed toward a light emitting element having improved luminous efficiency by including a surface-modified quantum dot in an emission layer.

One or more aspects of embodiments of the present disclosure are directed toward a method for manufacturing a light emitting element including a surface-modified quantum dot in an emission layer.

One or more example embodiments of the present disclosure provide a quantum dot composition including a quantum dot, and a ligand bonded to a surface of the quantum dot, wherein the ligand includes a head portion bonded to the surface of the quantum dot and containing a polar solvent dissociative functional group (e.g., a functional group that can dissolve in a polar solvent, or a polar functional group), and a tail portion connected to the head portion.

The head portion may include at least one selected from a sulfonyl ion, a carbonyl ion, a phosphate ion, an ammonium ion, an oxy group, and an amine group.

The quantum dot may include a core, and a shell surrounding the core (e.g., the quantum dot may have a core-shell structure).

The tail portion may include a substituted or unsubstituted alkyl group having 6 to 30 carbon atoms, or a substituted or unsubstituted aryl group having 6 to 30 ring-forming carbon atoms.

The ligand may be a monodentate ligand or a bidentate ligand.

The ligand may be represented by any one among Formulae 1 to 23:

$Na^+SO_3^- - R_1$ [Formula 1]

[Formula 2]

$H^+SO_3^- - R_1$ [Formula 3]

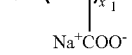
[Formula 4]

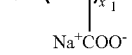
[Formula 5]

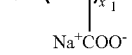
[Formula 6]

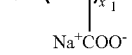
[Formula 7]

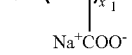
[Formula 8]

$Na^+COO^- - R_1$ [Formula 9]

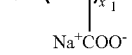
[Formula 10]

$H^+COO^- - R_1$ [Formula 11]

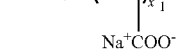
[Formula 12]

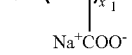
[Formula 13]

-continued

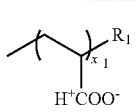
H⁺COO⁻

[Formula 14]

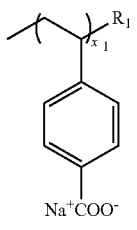
Na⁺COO⁻

[Formula 15]

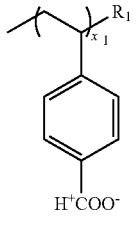
H⁺COO⁻

[Formula 16]

Na⁺PO₄⁻—R₁

[Formula 17]

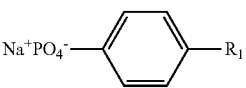
Na⁺PO₄⁻ —○— R₁

[Formula 18]

H⁺PO₄⁻—R₁

[Formula 19]

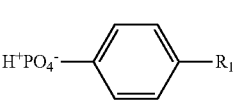
H⁺PO₄⁻ —○— R₁

[Formula 20]

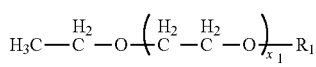
$H_3C-\overset{H_2}{C}-O-(\overset{H_2}{C}-\overset{H_2}{C}-O)_{x_1}-R_1$

[Formula 21]

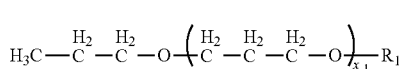
$H_3C-\overset{H_2}{C}-\overset{H_2}{C}-O-(\overset{H_2}{C}-\overset{H_2}{C}-\overset{H_2}{C}-O)_{x_1}-R_1$

[Formula 22]

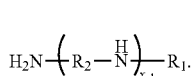
$H_2N-(R_2-\overset{H}{N})_{x_1}-R_1$.

[Formula 23]

In Formulae 1 to 23 above, $R_1$ and $R_2$ may each independently be a substituted or unsubstituted alkyl group having 7 to 30 carbon atoms, or a substituted or unsubstituted aryl group having 6 to 30 ring-forming carbon atoms, and xi may be an integer of 1 to 10.

The head portion may include a hydrogen cation ($H^+$), a sodium cation ($Na^+$), or a potassium cation ($K^+$).

The quantum dot composition according to an embodiment of the present disclosure may further include a non-polar organic solvent.

In an embodiment of the present disclosure, a light emitting element includes a first electrode, a hole transport region disposed on the first electrode, an emission layer disposed on the hole transport region and containing a quantum dot, an electron transport region disposed on the emission layer, and a second electrode disposed on the electron transport region.

The quantum dot may include a core and a shell surrounding the core.

The emission layer may further include ligand residues containing a polar solvent dissociative functional group.

The ligand residues may include at least one selected from a sulfonyl ion, a carbonyl ion, a phosphate ion, an ammonium ion, an oxy group, and an amine group.

The ligand residues may include a substituted or unsubstituted alkyl group having 6 to 30 carbon atoms, or a substituted or unsubstituted aryl group having 6 to 30 ring-forming carbon atoms.

The ligand residues may include a hydrogen cation, a sodium cation, or a potassium cation.

The ligand residues may include aliphatic or aromatic hydrocarbons connected to the polar solvent dissociative functional group.

One or more example embodiments of the present disclosure provide a method for manufacturing a light emitting element including: forming a first electrode, forming a hole transport region on the first electrode, providing, on the hole transport region, a quantum dot composition containing a quantum dot composite having a quantum dot and a ligand bonded to the surface thereof to form a preliminary emission layer, providing a polar solvent on the preliminary emission layer to form an emission layer, forming an electron transport region on the emission layer, and forming a second electrode on the electron transport region.

The ligand may include a head portion bonded to the surface of the quantum dot and containing a polar solvent dissociative functional group, and a tail portion connected to the head portion.

The providing of a polar solvent on the preliminary emission layer and the forming of an electron transport region on the emission layer may be performed in a single process (e.g., in the same process, concurrently, or simultaneously).

The providing of a polar solvent on the preliminary emission layer and the forming of an electron transport region on the emission layer may include applying, on the preliminary emission layer or the emission layer, a solution in which an electron transport material is dispersed in the polar solvent.

In the providing of a polar solvent on the preliminary emission layer, the ligand may be dissociated from the quantum dot through the polar solvent.

BRIEF DESCRIPTION OF THE DRAWINGS

The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings:

FIGS. 13 and 14 are cross-sectional views of a display device of an embodiment.

DETAILED DESCRIPTION

Figure 1:
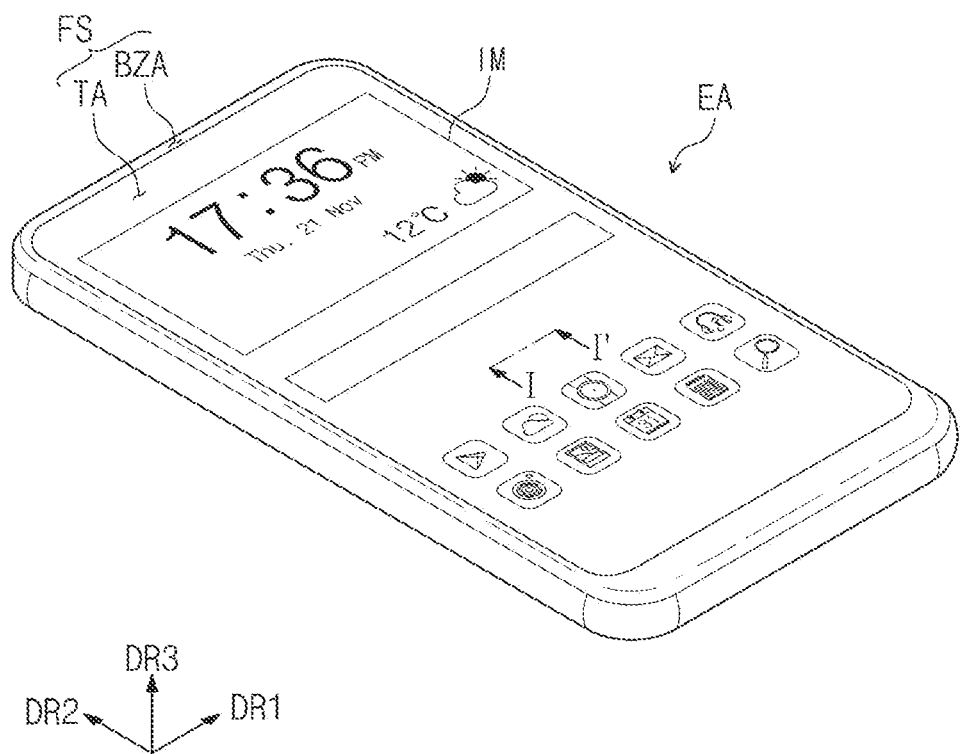
FIG. 1 is a perspective view of an electronic device of an embodiment.

The present disclosure may be modified in many alternate forms, example embodiments of which will be illustrated in the drawings and described in detail. It should be understood, however, that the description is not intended to limit the present disclosure to the particular forms disclosed, but rather, is intended to cover all modifications, equivalents, and alternatives falling within the spirit and scope of the present disclosure.

In the present description, when an element (or a region, a layer, a portion, etc.) is referred to as being "on," "connected to," or "coupled to" another element, it means that the element may be directly disposed on/connected to/coupled to the other element, or that one or more intervening elements may be disposed therebetween.

In the present disclosure, the term "directly disposed" indicates that no intervening element (such as a layer, film, region, plate and/or the like) is added between two reference elements. For example, "directly disposed" may refer to disposing two layers or elements adjacent to each other, without additional elements (such as an adhesive member) therebetween.

Like reference numerals refer to like elements throughout, and duplicative descriptions thereof may not be provided. In the drawings, the thickness, the ratio, and the dimensions of elements may be exaggerated for an effective description of technical contents.

The term "and/or," includes any and all combinations of one or more of the associated listed items. Further, the use of "may" when describing embodiments of the present disclosure refers to "one or more embodiments of the present disclosure".

It will be understood that, although the terms "first", "second", etc. may be used herein to describe various elements, these elements should not be limited by these terms. These terms are only used to distinguish one element from another. For example, a first element could be alternately termed a second element, and, similarly, a second element could be alternately termed a first element, without departing from the scope of example embodiments of the present disclosure. The terms of a singular form may include plural forms unless the context clearly indicates otherwise.

In addition, terms such as "below," "lower," "above," "upper," and/or the like are used to describe the relationship of the configurations shown in the drawings. The terms are used as a relative concept and are described with reference to the direction indicated in the drawings.

Unless otherwise defined, all terms (including technical and scientific terms) used herein have the same meaning as commonly understood by one of ordinary skill in the art to which the present disclosure pertains. It is also to be understood that terms defined in commonly used dictionaries should be interpreted as having meanings consistent with the meanings in the context of the related art, unless expressly defined herein, and should not be interpreted in an ideal or overly formal sense.

It should be understood that the terms "includes," "including," "have," "comprises," and/or "comprising," are intended to specify the presence of stated features, integers, steps, operations, elements, components, or combinations thereof in the disclosure, but do not preclude the presence or addition of one or more other features, integers, steps, operations, elements, components, or combinations thereof.

Hereinafter, a quantum dot composition according to an embodiment of the present disclosure, a light emitting element, and a display device including the same will be described with reference to the accompanying drawings.

Figure 2:
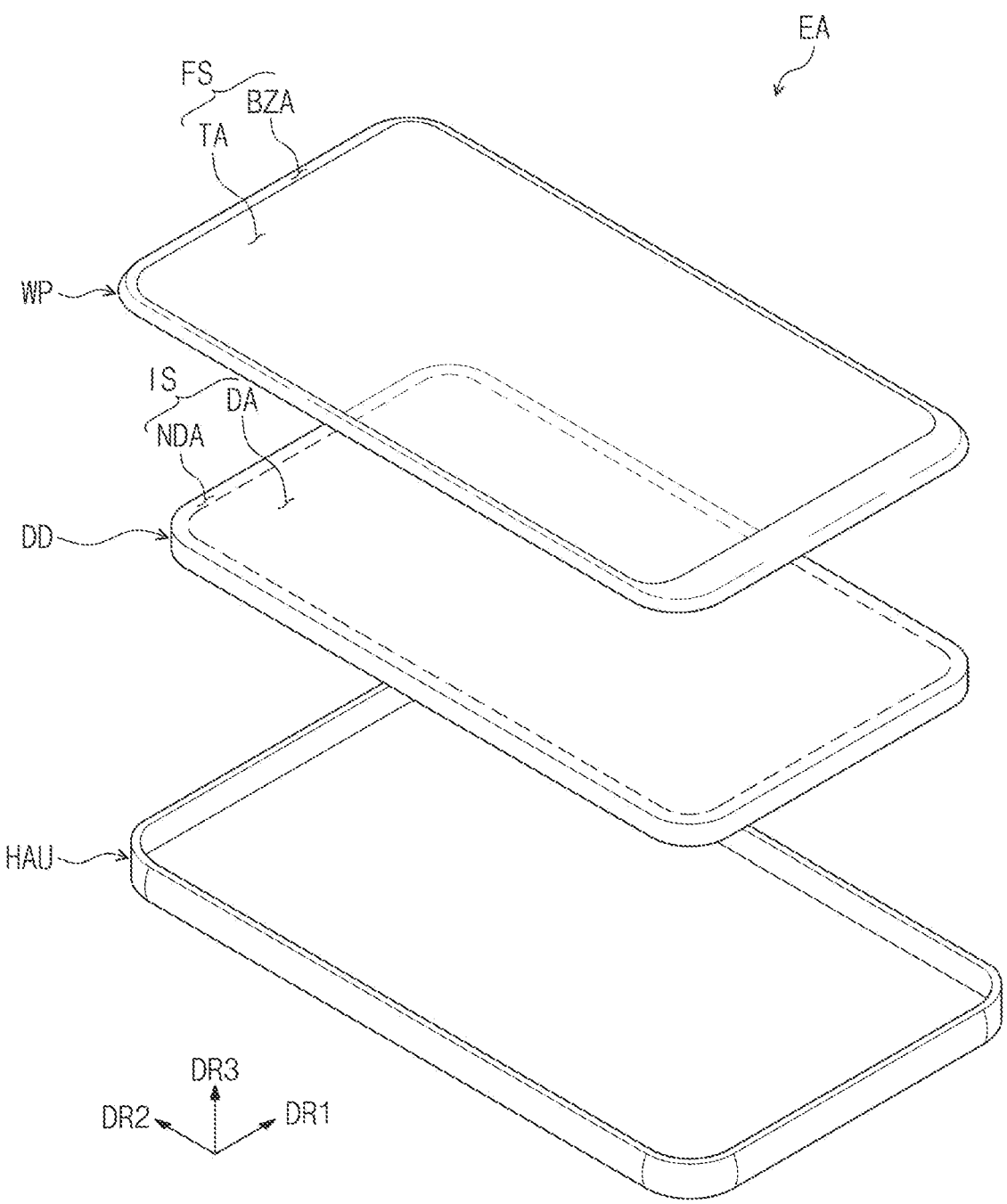
FIG. 2 is an exploded perspective view of an electronic device of an embodiment.
Figure 3:
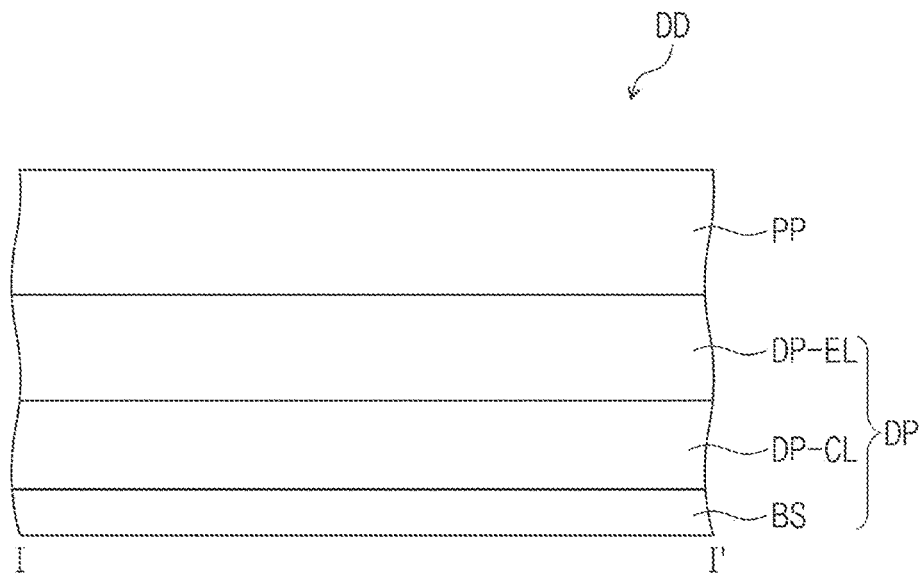
FIG. 3 is a cross-sectional view of a display device of an embodiment.
Figure 4:
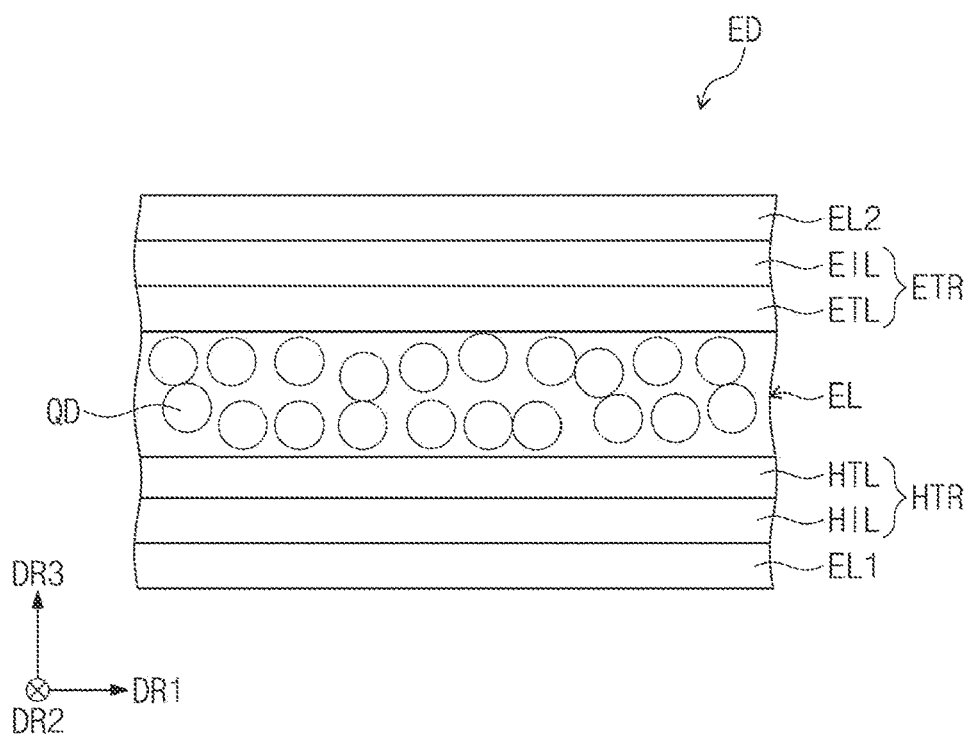
FIG. 4 is a cross-sectional view of a light emitting element of an embodiment.
Figure 5:
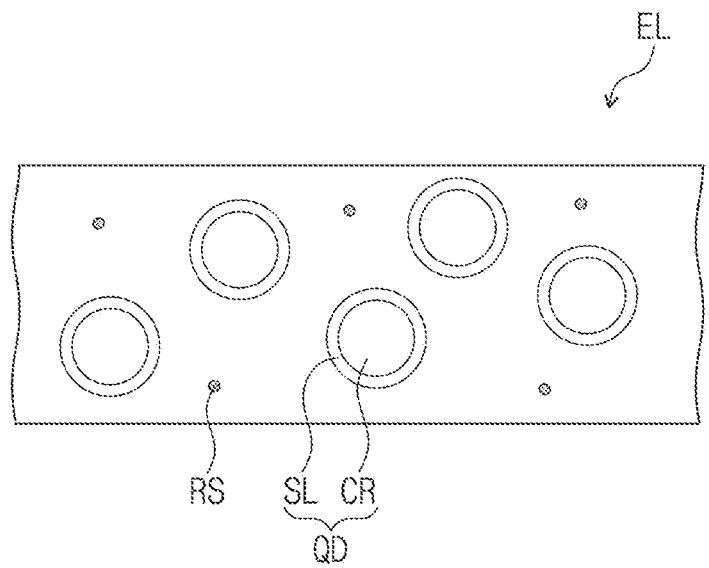
FIG. 5 is a cross-sectional view showing a part of emission layer of an embodiment.

FIG. 1 is a perspective view of an electronic device EA of an embodiment. FIG. 2 is an exploded perspective view of an electronic device EA of an embodiment. FIG. 3 is a cross-sectional view of a display device DD of an embodiment. FIG. 4 is a cross-sectional view of a light emitting element ED of an embodiment, and FIG. 5 is a cross-sectional view showing a part of an emission layer EL according to an embodiment.

In an embodiment, an electronic device EA may be a large-sized electronic device (such as a television set, a monitor, and/or an outdoor billboard). In some embodiments, the electronic device EA may be a small- or medium-sized electronic device (such as a personal computer, a laptop computer, a personal digital terminal, a car navigation unit, a game console, a smartphone, a tablet, and/or a camera). In addition to these examples, embodiments of the present disclosure may be adapted for other electronic devices without departing from the present disclosure. In the present embodiment, a smartphone is illustrated as an example electronic device EA.

The electronic device EA may include a display device DD and a housing HAU. The display device DD may display an image IM through (via) a display surface IS. FIG. 2 illustrates that the display surface IS parallel to (e.g., located on) a plane defined by a first direction DR1 and a second direction DR2 crossing the first direction DR1. However, this is presented as an example, and in another embodiment, the display surface IS of the display device DD may have a curved shape.

The image IM is displayed in a third direction DR3, which is along the direction normal to the display surface IS, for example, along the thickness direction of the display device DD. A front surface (or an upper surface) and a rear surface (or a lower surface) of each member may be defined by (e.g., with respect to position along) the third direction DR3.

A fourth direction DR4 (see FIG. 12) may be a direction between the first direction DR1 and the second direction DR2 (e.g., a diagonal direction in the plane formed by DR1 and DR2). For example, the fourth direction DR4 may be positioned on a plane parallel to the plane defined by the first direction DR1 and the second direction DR2. The directions indicated by the first to fourth directions DR1, DR2, DR3 and DR4 are relative concepts, and may thus be changed to other directions.

The display surface IS on which the image IM is displayed in the electronic device EA may correspond to (e.g., be on) a front surface of the display device DD and may correspond to (e.g., be congruent with) a front surface FS of a window WP. Hereinafter, like reference labels will be given for the display surface and the front surface of the electronic device EA and the display device DD, and the front surface of the window WP. The image IM may include a still image as well as a dynamic image. In some embodiments, the electronic device EA may include a foldable display device having a folding area and a non-folding area, or a bending display device having at least one bent portion.

The housing HAU may accommodate the display device DD. The housing HAU may be disposed to cover (e.g., hold or cradle) the display device DD such that an upper surface, which is the display surface IS of the display device DD, is exposed. The housing HAU may cover one or more side surfaces and a bottom surface of the display device DD, and expose the overall upper surface. However, embodiments of the present disclosure are not limited thereto, and in some embodiments, the housing HAU may cover a part of the upper surface as well as the side and bottom surfaces of the display device DD.

In the electronic device EA of an embodiment, the window WP may include an optically transparent insulating material. The window WP may include a transmission area TA and a bezel area BZA. The front surface FS of the window WP including the transmission area TA and the bezel area BZA corresponds to the front surface FS of the electronic device EA. A user may view an image provided through the transmission area TA corresponding to the front surface FS of the electronic device EA.

In the example of FIGS. 1 and 2, the transmission area TA is shown as a substantially rectangular shape with rounded vertices (corners). However, the transmission area TA may have any suitable shape, and is not limited to any one embodiment.

The transmission area TA may be an optically transparent area. The bezel area BZA may be an area having a relatively lower light transmittance than the transmission area TA. The bezel area BZA may have a set or predetermined color. The bezel area BZA may be adjacent to the transmission area TA and may surround (e.g., circumscribe) the transmission area TA. The bezel area BZA may define the shape of the transmission area TA. However, embodiments of the present disclosure are not limited to the illustrated example, and the bezel area BZA may be disposed adjacent only to one side of the transmission area TA, for example so that a portion thereof may be omitted.

The display device DD may be disposed under the window WP. In the present description, "below" or "under" may refer to a direction or position opposite the direction in which an image is provided by (projected from) the display device DD.

In an embodiment, the display device DD may be substantially configured to generate an image IM. The image IM generated in the display device DD is displayed on the display surface IS, and is viewed by a user through the transmission area TA from the outside. The display device DD includes a display area DA and a non-display area NDA. The display area DA may be an area activated with electrical signals. The non-display area NDA may be an area covered by the bezel area BZA. The non-display area NDA is adjacent to the display area DA. The non-display area NDA may surround (e.g., circumscribe) the display area DA.

The display device DD may include a display panel DP and a light control layer PP disposed on the display panel DP. The display panel DP may include a display element layer DP-EL. The display element layer DP-EL includes a light emitting element ED (e.g., see FIGS. 4 and 13).

Figure 13:
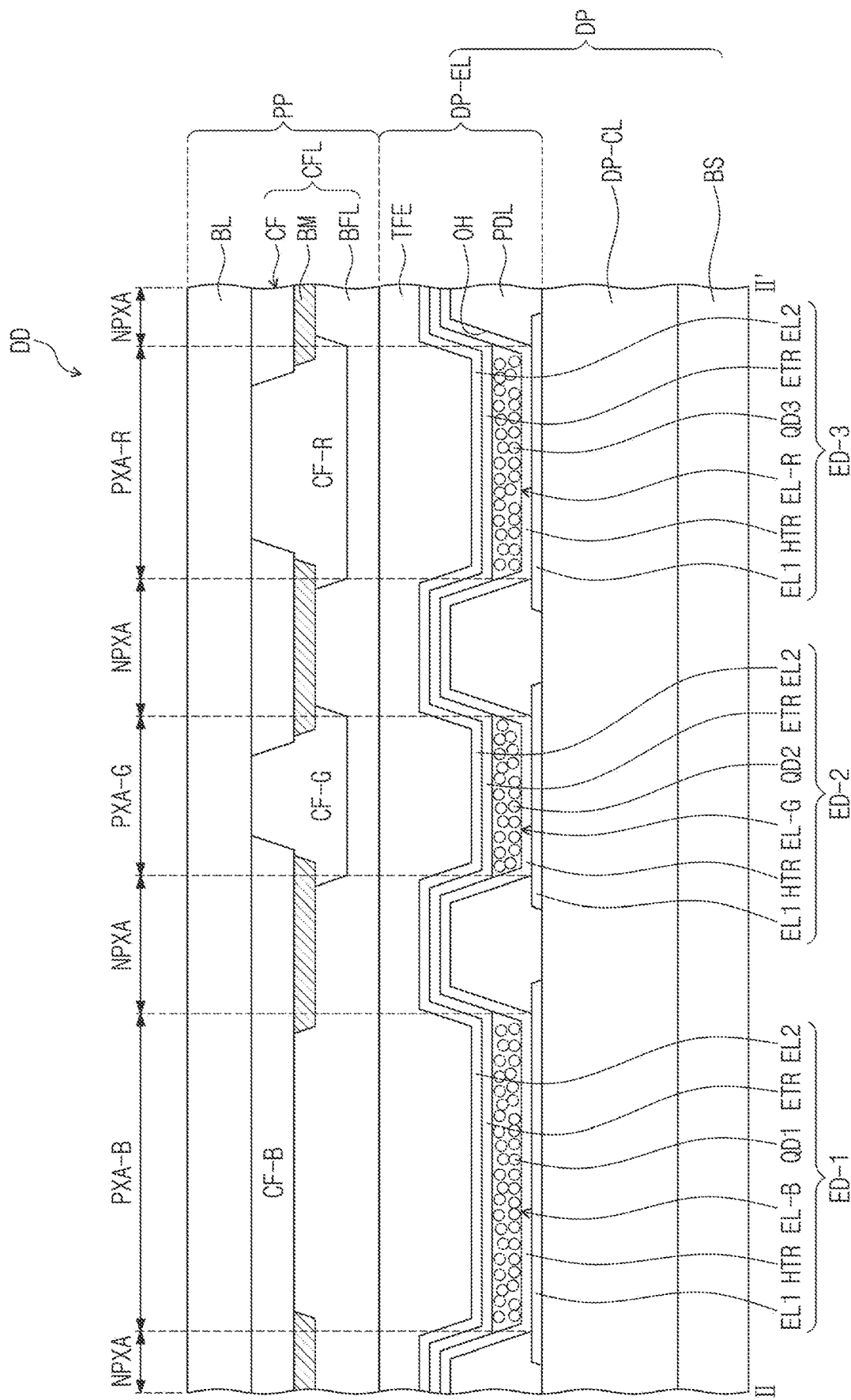

The display device DD may include a plurality of light emitting elements ED-1, ED-2, and ED-3 (see FIG. 13). The light control layer PP may be disposed on the display panel DP to control reflected light from the display panel DP due to external light. The light control layer PP may include, for example, a polarizing layer or a color filter layer.

In the display device DD of an embodiment, the display panel DP may be a light emitting display panel. For example, the display panel DP may be a quantum dot light emitting display panel including a quantum dot light emitting element. However, embodiments of the present disclosure are not limited thereto.

The display panel DP may include a base substrate BS, a circuit layer DP-CL disposed on the base substrate BS, and a display element layer DP-EL disposed on the circuit layer DP-CL.

The base substrate BS may be a member providing a base surface, on which the display element layer DP-EL is disposed. The base substrate BS may be a glass substrate, a metal substrate, a plastic substrate, etc. However, embodiments of the present disclosure are not limited thereto, and the base substrate BS may be an inorganic layer, an organic layer or a composite material layer. In some embodiments, the base substrate BS may be a flexible substrate that may be readily bent or folded.

In an embodiment, the circuit layer DP-CL may be disposed on the base substrate BS (e.g., between the base substrate BS and the display element layer DP-EL), and the circuit layer DP-CL may include a plurality of transistors. The transistors may each include a control electrode, an input electrode, and an output electrode. For example, the circuit layer DP-CL may include a switching transistor and a driving transistor to drive the light emitting element ED of the display element layer DP-EL.

FIG. 4 is a view showing a light emitting element ED according to an embodiment, and referring to FIG. 4, the light emitting element ED according to an embodiment includes a first electrode EL1, a second electrode EL2 facing the first electrode EL1, and a plurality of functional layers disposed between the first electrode EL1 and the second electrode EL2 and having an emission layer EL.

The plurality of functional layers may include a hole transport region HTR disposed between the first electrode EL1 and the emission layer EL, and an electron transport region ETR disposed between the emission layer EL and the second electrode EL2. In some embodiments, a capping layer may be further disposed on the second electrode EL2.

The hole transport region HTR and the electron transport region ETR each may include a plurality of sub functional layers. For example, the hole transport region HTR may include a hole injection layer HIL and a hole transport layer HTL as sub functional layers, and the electron transport region ETR may include an electron injection layer EIL and an electron transport layer ETL as sub functional layers. Embodiments of the present disclosure are not limited thereto, and the hole transport region HTR may further include an electron blocking layer as a sub functional layer, and the electron transport region ETR may further include a hole blocking layer as a sub functional layer.

In the light emitting element ED according to an embodiment, the first electrode EL1 has conductivity. The first electrode EL1 may be formed of a metal alloy or a conductive compound. The first electrode EL1 may be an anode. The first electrode EL1 may be a pixel electrode.

In the light emitting element ED according to an embodiment, the first electrode EL1 may be a reflective electrode. However, embodiments of the present disclosure are not limited thereto. For example, the first electrode EL1 may be a transmissive electrode, or a transflective electrode. When the first electrode EL1 is a transmissive electrode, the first electrode EL1 may be formed of a transparent metal oxide, for example, indium tin oxide (ITO), indium zinc oxide (IZO), zinc oxide (ZnO), indium tin zinc oxide (ITZO), etc.

When the first electrode EL1 is a transflective electrode or a reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), ytterbium (Yb), a compound thereof, or a mixture thereof (e.g., a mixture of Ag and Mg). In some embodiments, the first electrode EL1 may have a multi-layer structure including a reflective film or a transflective film formed of the materials described above as an example, and a transparent conductive film formed of indium tin oxide (ITO), indium zinc oxide (IZO), zinc oxide (ZnO), indium tin zinc oxide (ITZO), etc. For example, the first electrode EL1 may be a multi-layer metal film, and may have a stacked structure of metal films of ITO/Ag/ITO.

The hole transport region HTR is provided on the first electrode EL1. The hole transport region HTR may include a hole injection layer HIL, a hole transport layer HTL, etc. In addition, the hole transport region HTR may further include at least one of a hole buffer layer or an electron blocking layer EBL in addition to the hole injection layer HIL and the hole transport layer HTL. The hole buffer layer may compensate a resonance distance of the wavelength of light emitted from an emission layer EL, and may thus increase luminous efficiency. Materials included in the hole transport region HTR may also be used as materials included in the hole buffer layer. The electron blocking layer may prevent or reduce electrons from being injected from the electron transport region ETR to the hole transport region HTR.

The hole transport region HTR may have a single layer formed of a single material, a single layer formed of a plurality of different materials, or a multi-layer structure including a plurality of layers formed of a plurality of different materials. For example, the hole transport region HTR may have a single-layer structure formed of a plurality of different materials, or a structure in which a hole injection layer HIL/hole transport layer HTL, a hole injection layer HIL/hole transport layer HTL/hole buffer layer, a hole injection layer HIL/hole buffer layer, a hole transport layer HTL/hole buffer layer, or a hole injection layer HIL/hole transport layer HTL/electron blocking layer EBL are stacked in order from the first electrode EL1, but embodiments are not limited thereto.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

The hole injection layer HIL may include, for example, a phthalocyanine compound such as copper phthalocyanine, N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino]triphenylamine (m-MTDATA), 4,4',4"-tris(N,N-diphenylamino)triphenylamine (TDATA), 4,4',4"-tris{N-(2-naphthyl)-N-phenylamino}-triphenylamine (2-TNATA), poly(3,4-ethylene dioxythiophene)/poly(4-styrene sulfonate) (PEDOT/PSS), polyaniline/dodecylbenzene sulfonic acid (PANI/DBSA), polyaniline/camphor sulfonic acid (PANI/CSA), polyaniline/poly(4-styrene sulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may include, for example, carbazole-based derivatives (such as N-phenyl carbazole and/or polyvinyl carbazole), fluorene-based derivatives, N,N'-bis(3-methylphenyl)-N,N'-diphenyl-[1,1-biphenyl]-4, 4'-diamine (TPD), triphenylamine-based derivatives (such as 4,4',4"-tris(N-carbazolyl)triphenylamine (TCTA)), N,N'-di(naphthalen-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), 1,3-bis(N-carbazolyl)benzene (mCP), etc.

The emission layer EL is provided on the hole transport region HTR. In the light emitting element ED according to an embodiment, the emission layer EL may include a quantum dot QD. The quantum dot QD may include a core CR and a shell SL surrounding the core CR.

The emission layer EL in the light emitting element ED of an embodiment may be formed from a quantum dot composition of an embodiment. The quantum dot composition of an embodiment includes a quantum dot and a ligand bonded to a quantum dot surface.

The emission layer EL may include a plurality of quantum dots QD. The quantum dots QD included in the emission layer EL may be stacked to form one or more layers. In FIG. 4, for example, quantum dots QD having circular cross-sections are arranged to form two layers, but embodiments are not limited thereto. For example, the arrangement of the quantum dots QD may vary according to the thickness of the emission layer EL, the shape of the quantum dots QD included in the emission layer EL, and the average diameter of the quantum dots QD. For example, in the emission layer EL, the quantum dots QD may adjacently align to form a single layer, or may align to form a plurality of layers (such as two or three layers).

The emission layer EL may have, for example, a thickness of about 5 nm to about 20 nm, or about 10 nm to about 20 nm.

As described above, the emission layer EL includes quantum dots QD formed from the quantum dot composition of an embodiment. In some embodiments, the emission layer EL may include a small amount of ligand residues RS derived from the ligand of the quantum dot composition of an embodiment. The ligand residues RS dissociate from the surface of the quantum dot composition, for example, by dissolving in a polar solvent. The ligand residues RS may include a polar solvent dissociative functional group. In an embodiment, the ligand residues RS may include an anionic group (such as a sulfonyl ion, a carbonyl ion, and/or a phosphate ion), and a cationic group (such as a hydrogen cation, a sodium cation, or a potassium cation) as a counterion of the anionic group. The ligand residues RS may include aliphatic or aromatic hydrocarbons connected to the polar solvent dissociative functional group.

The quantum dot QD included in the emission layer EL of an embodiment may be a semiconductor nanocrystal selected from a Group II-VI compound, a Group III-V compound, a Group IV-VI compound, a Group IV element, a Group IV compound, and a combination thereof.

The Group II-VI compound may be selected from the group consisting of a binary compound selected from the group consisting of CdS, CdSe, CdTe, ZnS, ZnSe, ZnTe, ZnO, HgS, HgSe, HgTe, MgSe, MgS, and a mixture thereof, a ternary compound selected from the group consisting of AgInS, CuInS, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and a mixture thereof, and a quaternary compound selected from the group consisting of HgZnTeS, CdZnSeS, CdZnSeTe, CdZnSTe, CdHgSeS, CdHgSeTe, CdHgSTe, HgZnSeS, HgZnSeTe, HgZnSTe, and a mixture thereof.

The Group III-V compound may be selected from the group consisting of a binary compound selected from the group consisting of GaN, GaP, GaAs, GaSb, AlN, AlP, AlAs, AlSb, InN, InP, InAs, InSb, and a mixture thereof, a ternary compound selected from the group consisting of GaNP, GaNAs, GaNSb, GaPAs, GaPSb, AlNP, AlNAs, AlNSb, AlPAs, AlPSb, InGaP, InNP, InNAs, InNSb, InPAs, InPSb, and a mixture thereof, and a quaternary compound selected from the group consisting of GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and a mixture thereof.

The Group IV-VI compound may be selected from the group consisting of a binary compound selected from the group consisting of SnS, SnSe, SnTe, PbS, PbSe, PbTe, and a mixture thereof, a ternary compound selected from the group consisting of SnSeS, SnSeTe, SnSTe, PbSeS, PbSeTe, PbSTe, SnPbS, SnPbSe, SnPbTe, and a mixture thereof, and a quaternary compound selected from the group consisting of SnPbSSe, SnPbSeTe, SnPbSTe, and a mixture thereof. The Group IV element may be selected from the group consisting of Si, Ge, and a mixture thereof. The Group IV compound may be a binary compound selected from the group consisting of SiC, SiGe, and a mixture thereof.

The binary compound, the ternary compound, or the quaternary compound may be present in a particle in a substantially uniform (e.g., homogenous) concentration distribution, or may be present in the same particle in a partially different (e.g., heterogenous) concentration distribution. In addition, a core/shell structure in which one quantum dot surrounds another quantum dot may be present. An interface between a core and a shell may have a concentration gradient in which the concentration of an element present in a shell becomes lower toward the center.

In some embodiments, a quantum dot QD may have a core/shell structure including a core CR having nano-crystals, and a shell SL surrounding the core CR, which are described above. The shell SL of the core/shell quantum dot QD may serve as a protection layer to prevent or reduce chemical deformation of the core CR so as to maintain its semiconductor properties, and/or may serve as a charging layer to impart electrophoretic properties to the quantum dot QD. The shell SL may be a single layer or may have multiple layers. An interface between the core CR and the shell SL may have a concentration gradient in which the concentration of an element present in the shell SL becomes lower toward the center (e.g., in the core CR). An example of the shell SL of the quantum dot QD having the core/shell structure may be a metal or non-metal oxide, a semiconductor compound, or a combination thereof.

For example, the metal or non-metal oxide may be a binary compound such as $SiO_2$, $Al_2O_3$, $TiO_2$, ZnO, MnO, $Mn_2O_3$, $Mn_3O_4$, CuO, FeO, $Fe_2O_3$, $Fe_3O_4$, CoO, $Co_3O_4$, and/or NiO, or a ternary compound such as $MgAl_2O_4$, $CoFe_2O_4$, $NiFe_2O_4$, and/or $CoMn_2O_4$, but embodiments of the present disclosure are not limited thereto.

In addition, the semiconductor compound may be, for example, CdS, CdSe, CdTe, ZnS, ZnSe, ZnTe, ZnSeS, ZnTeS, GaAs, GaP, GaSb, HgS, HgSe, HgTe, InAs, InP, InGaP, InSb, AlAs, AlP, AlSb, etc., but embodiments of the present disclosure are not limited thereto.

A quantum dot QD may have a full width at half maximum (FWHM) of a light emission wavelength spectrum of about 45 nm or less, for example, about 40 nm or less, for example, about 30 nm or less, and color purity or color reproducibility may be enhanced in the above range. In addition, the light emitted by such a quantum dot is emitted in all directions, and thus a wide viewing angle may be improved.

The shape or form of the quantum dot QD is not particularly limited and may be any form available in the art, and may be or include, for example, spherical, pyramidal, multi-arm, or cubic nanoparticles, nanotubes, nanowires, nanofibers, nanoparticles, etc.

The color of emitted light depends on the particle size of the quantum dot QD, and thus the quantum dot QD may be selected to have a suitable light emission color (such as blue, red, green, etc.) The smaller the particle size of the quantum dot QD, the shorter the wavelength of emitted light. For example, in the quantum dot QD having the same core CR, the particle size of a quantum dot emitting green light may be smaller than the particle size of a quantum dot emitting red light. In addition, in the quantum dot QD having the same core, the particle size of a quantum dot emitting blue light may be smaller than the particle size of a quantum dot emitting green light. However, embodiments of the present disclosure are not limited thereto, and even in the quantum dot QD having the same core, the particle size may be adjusted according to the composition and thickness of a shell.

When multiple quantum dots QD have different light emission colors (such as blue, red, green, etc.), the quantum dots QD may have different core materials.

In some embodiments, in the light emitting element ED of an embodiment, an emission layer EL may include a host and a dopant. In an embodiment, the emission layer EL may include a quantum dot QD as a dopant material. In addition, in an embodiment, the emission layer EL may further include a host material.

In the light emitting element ED of an embodiment, an emission layer EL may be to emit fluorescence. For example, a quantum dot QD may be used as a fluorescent dopant material.

The emission layer EL may be formed using any suitable method (such as a vacuum deposition method, a spin coating method, a cast method, a Langmuir-Blodgett (LB) method, an inkjet printing method, a laser printing method, a laser induced thermal imaging (LITI) method, etc.)

In the light emitting element ED of an embodiment, an electron transport region ETR is provided on the emission layer EL. The electron transport region ETR may include at least one among a hole blocking layer, an electron transport layer ETL, and an electron injection layer EIL, but embodiments of the present disclosure are not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of an electron injection layer EIL or an electron transport layer ETL, or may have a single layer structure formed of an electron injection material and an electron transport material. In some embodiments, the electron transport region ETR may have a single layer structure formed of a plurality of different materials, or may have a structure in which an electron transport layer ETL/electron injection layer EIL, and a hole blocking layer/electron transport layer ETL/electron injection layer EIL are stacked in order from the emission layer EL, but embodiments of the present disclosure are not limited thereto. The thickness of the electron transport region ETR may be, for example, about 200 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, a laser induced thermal imaging (LITI) method, etc.)

When the electron transport region ETR includes the electron transport layer ETL, the electron transport region ETR may include an anthracene-based compound. However, embodiments of the present disclosure are not limited thereto, and the electron transport region ETR may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzimidazol-1-yl)phenyl)-9,10-dinaphthylanthracene, 1,3,5-tri (1-phenyl-1H-benz[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato)aluminum (BAlq), beryllium bis(benzoquinolin-10-olate) ($Bebq_2$), 9,10-di(naphthalen-2-yl) anthracene (ADN), or a mixture thereof. In some embodiments, the electron transport layer ETL may include a metal oxide such as ZnO. The thickness of the electron transport layer ETL may be about 100 Å to about 1,000 Å and may be, for example, about 150 Å to about 500 Å. When the thicknesses of the electron transport layers ETL satisfy the above-described range, satisfactory electron transport properties may be obtained without a substantial increase in driving voltage.

When the electron transport region ETR includes the electron injection layer EIL, the electron transport region ETR may include a halogenated metal, a metal oxide, a lanthanide metal, or a co-deposited material of a halogenated metal and a lanthanide metal. In some embodiments, the halogenated metal may be an alkali metal halide. For example, the electron transport region ETR may include LiF, lithium quinolate (LiQ), $Li_2O$, BaO, NaCl, CsF, Yb, RbCl, RbI, KI, CuI, or KI:Yb, but the embodiment of the present disclosure is not limited thereto. The electron injection layer EIL may also be formed of a mixture material of an electron injection material and an insulating organo-metal salt. The insulating organo-metal salt may include, for example, metal acetates, metal benzoates, metal acetoacetates, metal acetylacetonates, and/or metal stearates. The thicknesses of the electron injection layers EIL may be about 1 Å to about 100 Å, and about 3 Å to about 90 Å. When the thicknesses of the electron injection layers EIL satisfy the above-described range, satisfactory electron injection properties may be obtained without a substantial increase in driving voltage.

The electron transport region ETR may include a hole blocking layer as described above. The hole blocking layer may include, for example, at least one of 2,9-dimethyl-4,7-diphenyl-1,10-phenanthroline (BCP) or 4,7-diphenyl-1,10-phenanthroline (Bphen), but is not limited thereto.

The second electrode EL2 is provided on the electron transport region ETR. The second electrode EL2 may be a common electrode or a cathode. The second electrode EL2 may be a transmissive electrode, a transflective electrode or a reflective electrode. When the second electrode EL2 is a transmissive electrode, the second electrode EL2 may be formed of a transparent metal oxide, for example, indium tin oxide (ITO), indium zinc oxide (IZO), zinc oxide (ZnO), indium tin zinc oxide (ITZO), etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, Yb, a compound thereof, or a mixture thereof (e.g., a mixture of Ag and Mg). For example, the second electrode EL2 may include AgMg, AgYb, and/or MgAg. In some embodiments, the second electrode EL2 may have a multilayer structure including a reflective film or a transflective film formed of the above-described materials, and a transparent conductive film formed of indium tin oxide (ITO), indium zinc oxide (IZO), zinc oxide (ZnO), indium tin zinc oxide (ITZO), etc.

In some embodiments, the second electrode EL2 may be connected with an auxiliary electrode. When the second electrode EL2 is connected with the auxiliary electrode, the resistance of the second electrode EL2 may decrease.

Figure 6:
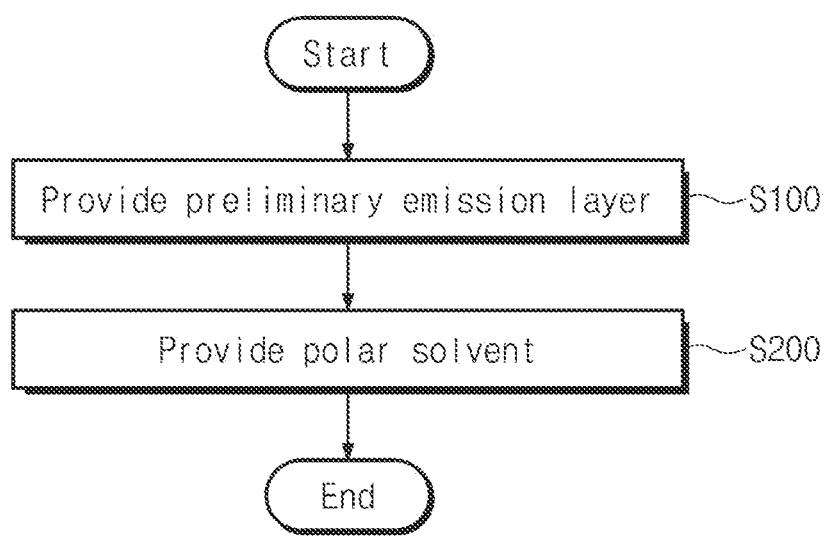
FIG. 6 is a flowchart showing a method for manufacturing a light emitting element according to an embodiment.
Figure 7:
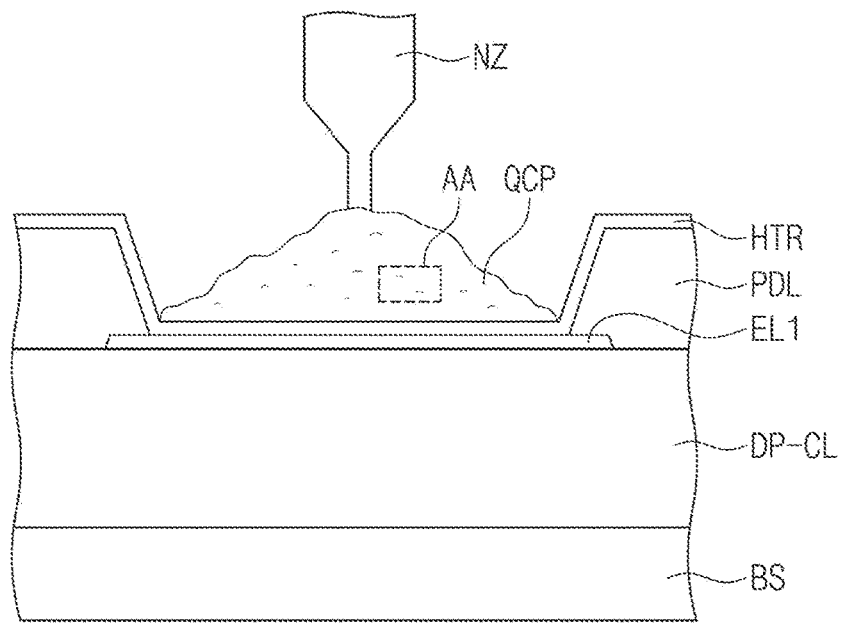
FIG. 7 is a schematic view illustrating an act in a method for manufacturing a light emitting element according to an embodiment.
Figure 8:
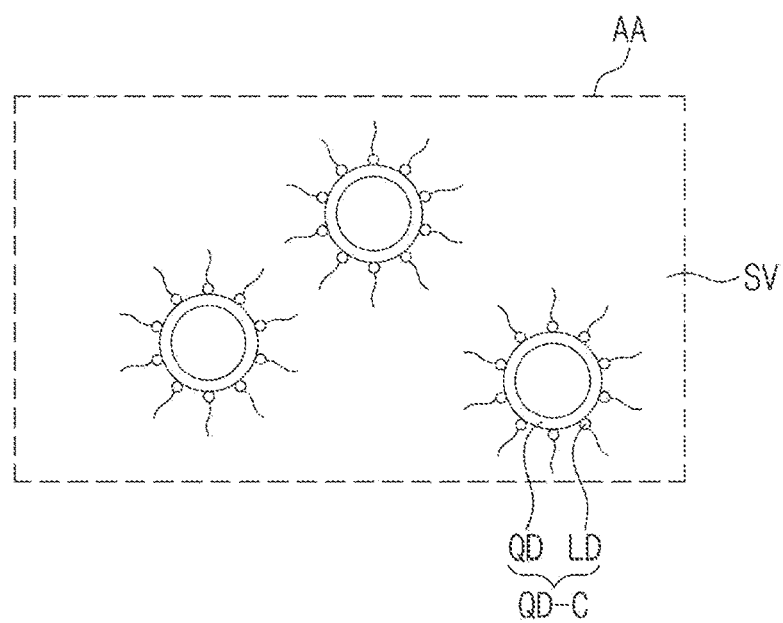
FIG. 8 is a schematic view illustrating a quantum dot composition according to an embodiment.
Figure 9:
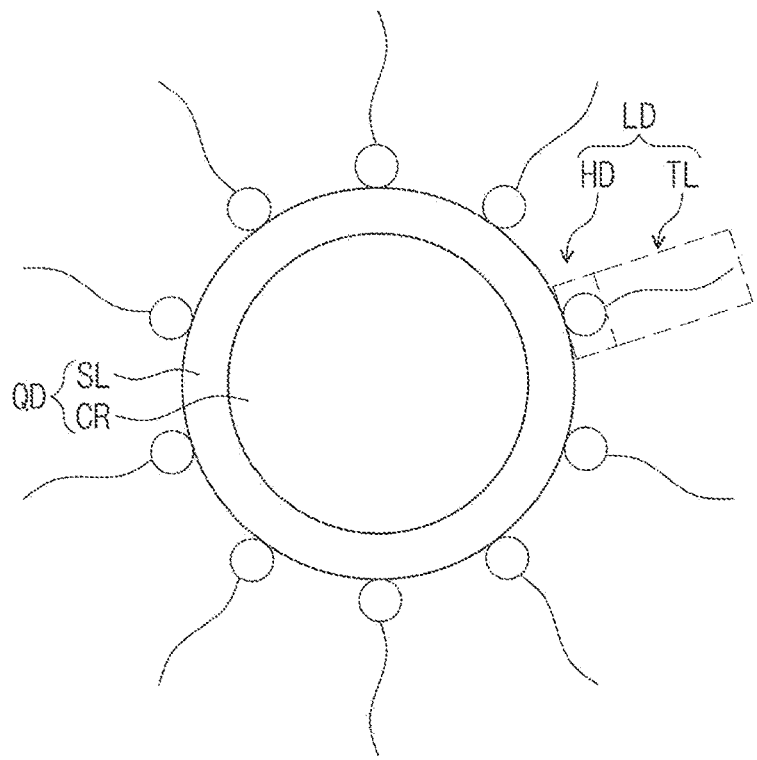
FIG. 9 is a schematic view illustrating a quantum dot and a ligand included in a quantum dot composition of an embodiment.
Figure 10:
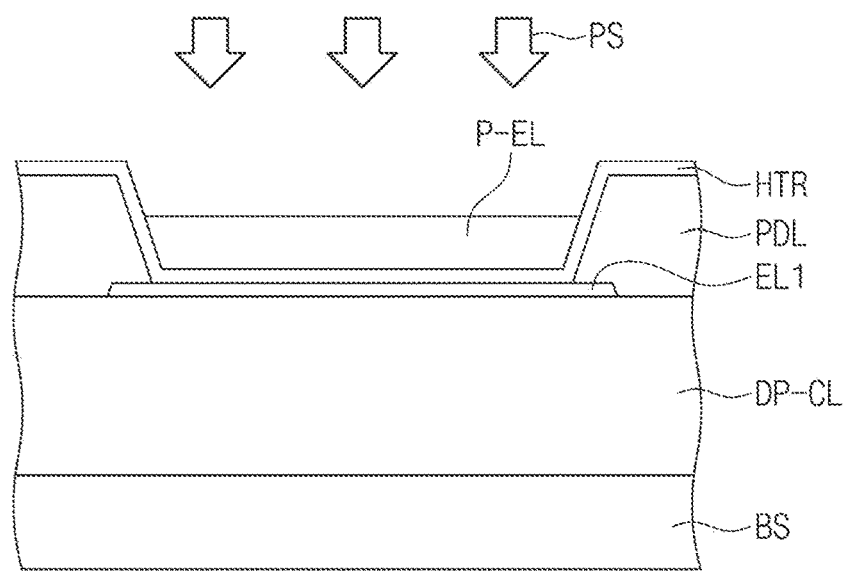
FIG. 10 is a schematic view illustrating an act in a method for manufacturing a light emitting element according to an embodiment.

FIG. 6 is a flowchart illustrating at least a part of a method for manufacturing a light emitting element according to an embodiment. FIG. 7 is a schematic view illustrating an act in the method for manufacturing a light emitting element according to an embodiment. FIG. 8 is a schematic view illustrating a quantum dot composition according to an embodiment. FIG. 9 is a schematic view illustrating a quantum dot and a ligand included in a quantum dot composition of an embodiment. FIG. 10 is a schematic view illustrating an act in the method for manufacturing a light emitting element according to an embodiment.

The forming of an emission layer in the method for manufacturing a light emitting element according to an embodiment may include providing a preliminary emission layer (S100), and providing a polar solvent to form an emission layer (S200).

FIG. 7 is a schematic view showing the forming of an emission layer in a method for manufacturing a light emitting element according to an embodiment. The forming of an emission layer may include providing a quantum dot composition QCP on a hole transport region HTR. The quantum dot composition QCP may be provided to a region between a pixel defining film PDL through a nozzle NZ.

FIG. 8 is a view illustrating a part (region "AA") of a quantum dot composition QCP provided in FIG. 7 in more detail. FIG. 9 is a schematic view illustrating a quantum dot composite QD-C including a structure in which a ligand LD is bonded to a surface of a quantum dot QD. FIG. 9 is a schematic view illustrating a bonding relationship of a structure in which a ligand LD is bonded to a surface of a quantum dot QD in a quantum dot composition.

Referring to FIGS. 7 to 9, a quantum dot composition QCP of an embodiment may include a quantum dot QD, and a ligand LD bonded to a quantum dot QD surface. The quantum dot composition QCP may further include a non-polar organic solvent SV in which the quantum dot QD and the ligand LD are dispersed. For example, the non-polar organic solvent may include hexane, toluene, chloroform, dimethyl sulfoxide, dimethyl formamide, etc. However, embodiments of the present disclosure are not limited thereto. The non-polar organic solvent SV may include or refer to aliphatic or aromatic hydrocarbons having a sum of dP and dH in a Hansen Solubility Parameter (HSP) of 2 or less.

The quantum dot QD may be provided by being dispersed in the non-polar organic solvent SV. The ligand LD may be bonded to the surface of the quantum dot QD to increase the dispersibility of the quantum dot composite QD-C in the non-polar organic solvent SV. In the act of forming of an emission layer, applying heat to evaporate the non-polar organic solvent SV may be further included after the providing of the quantum dot composition QCP. The evaporating of the non-polar organic solvent SV may be performed in a single process together with the applying of heat to dissociate the ligand LD (e.g., the same process or simultaneously).

As described above, the quantum dot QD may include a core CR and a shell SL surrounding the core CR. However, embodiments of the present disclosure are not limited thereto, and the quantum dot QD may have a single-layer structure or a plurality of shells. The description on the quantum dot QD in the light emitting element ED of an embodiment described with reference to FIGS. 4 and 5 may be applied to a quantum dot QD included in the quantum dot composition QCP of an embodiment.

The ligand LD includes a head portion HD bonded to a surface of the quantum dot QD, and a tail portion TL. The head portion HD is bonded to the surface of the quantum dot QD, and may include a functional group to bind to the surface of the quantum dot QD. The head portion HD includes a polar solvent dissociative functional group (e.g., a functional group capable of dissolving in a polar solvent) as a functional group to bind to the surface of the quantum dot QD. The head portion HD may include a polar material having a property of being dissociated from the surface of the quantum dot QD by a polar solvent PS (see FIG. 10) which will be described later. The head portion HD may include an ionic material, or a functional group having strong polarity (such as an oxy group and an amine group). In an embodiment, the head portion HD of the ligand LD may include a sulfonyl anion, a carbonyl anion, a phosphate anion, etc. and a counter cation complex corresponding thereto. In an embodiment, the head portion HD of the ligand LD may include an alkyl oxy group or an alkyl amine group. When the head portion HD includes a single functional group to bind to the surface of the quantum dot QD, the ligand LD may be a monodentate ligand. When the head portion HD includes two functional groups to bind to the surface of the quantum dot QD, the ligand LD may be a bidentate ligand. The head portion HD may include a functional group to bind to the surface of a shell SL of the quantum dot QD.

The tail portion TL is connected to the head portion HD and may include a non-polar organic material to secure dispersibility of a quantum dot composite QD-C in a non-polar organic solvent SV. In an embodiment, the tail portion TL may include a substituted or unsubstituted alkyl group having 7 to 30 carbon atoms, or a substituted or unsubstituted aryl group having 6 to 30 ring-forming carbon atoms. For example, the tail portion TL may include a substituted or unsubstituted phenyl group.

In the quantum dot composition QCP of an embodiment, the ligand LD may be represented by any one among Formulae 1 to 23:

$$Na^+SO_3^- - R_1 \quad \text{[Formula 1]}$$

$$Na^+SO_3^- - \phenyl - R_1 \quad \text{[Formula 2]}$$

$$H^+SO_3^- - R_1 \quad \text{[Formula 3]}$$

$$H^+SO_3^- - \phenyl - R_1 \quad \text{[Formula 4]}$$

[Formula 5] (alkyl chain with $R_1$ and $Na^+SO_3^-$)

[Formula 6] (alkyl chain with $R_1$ and $H^+SO_3^-$)

[Formula 7] (alkyl chain with $R_1$ and phenyl-$Na^+SO_3^-$)

[Formula 8] (alkyl chain with $R_1$ and phenyl-$H^+SO_3^-$)

$$Na^+COO^- - R_1 \quad \text{[Formula 9]}$$

$$Na^+COO^- - \phenyl - R_1 \quad \text{[Formula 10]}$$

$$H^+COO^- - R_1 \quad \text{[Formula 11]}$$

$$H^+COO^- - \phenyl - R_1 \quad \text{[Formula 12]}$$

[Formula 13] (alkyl chain with $R_1$ and $Na^+COO^-$)

[Formula 14] (alkyl chain with $R_1$ and $H^+COO^-$)

[Formula 15] (alkyl chain with $R_1$ and phenyl-$Na^+COO^-$)

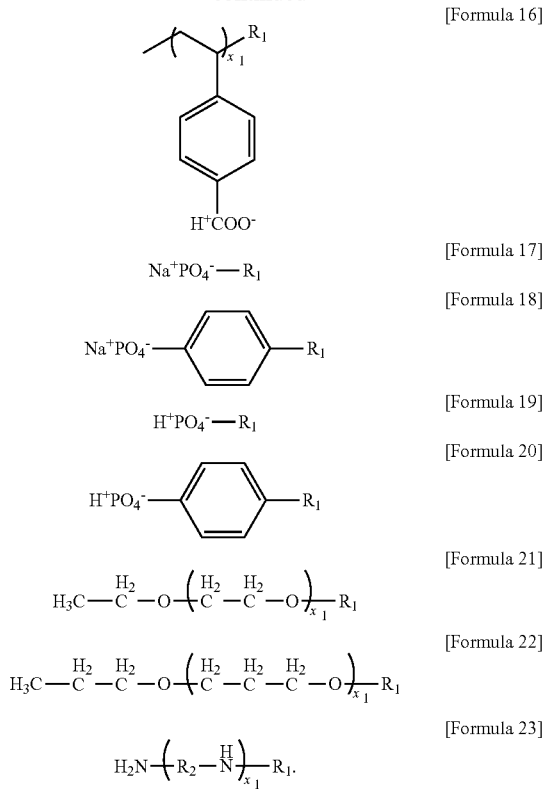

In Formulae 1 to 23, $R_1$ may be a substituted or unsubstituted alkyl group having 7 to 30 carbon atoms, or a substituted or unsubstituted aryl group having 6 to 30 ring-forming carbon atoms. In Formulae 1 to 23, $x_1$ may be an integer of 1 to 10.

In the present description, the term "substituted or unsubstituted" may indicate that one (group or atom) is unsubstituted, or is substituted with at least one substituent selected from the group consisting of a deuterium atom, a halogen atom, a cyano group, a nitro group, an amine group, a silyl group, oxy group, thio group, sulfinyl group, sulfonyl group, carbonyl group, a boron group, a phosphine oxide group, a phosphine sulfide group, an alkyl group, an alkenyl group, an alkoxy group, an aliphatic hydrocarbon ring group, an aryl group, and a heterocyclic group. Each of the example substituents may be further substituted or unsubstituted. For example, a biphenyl group may be interpreted as a named aryl group, or as a phenyl group substituted with a phenyl group.

FIG. 10 is a schematic view illustrating the act of forming an emission layer by providing a polar solvent (S200) in a method for manufacturing a light emitting element according to an embodiment. FIG. 10 shows providing a polar solvent PS to a preliminary emission layer P-EL.

Referring to FIGS. 8 to 10 together, the providing of a polar solvent PS may include adding the polar solvent PS to a quantum dot composite QD-C included in a preliminary emission layer P-EL to dissociate a ligand LD bonded to a surface of the quantum dot QD. The ligand LD is bonded to the surface of the quantum dot QD in a non-polar organic solvent SV, and when the polar solvent PS is added, the bond between the head portion HD of the ligand LD and the quantum dot QD is removed and dissociated.

In an embodiment, the providing of the polar solvent PS is not performed alone, but may be performed in the same single process together with forming another layer through a subsequent process on the emission layer. In an embodiment, the providing of the polar solvent PS may be performed in the same single process together with forming an electron transport region ETR (FIG. 4) on the emission layer. For example, the providing of the polar solvent PS may be performed by dispersing a metal oxide such as ZnO as an electron transport material in a polar solvent such as ethanol, and spin coating the resultant on the preliminary emission layer P-EL.

The polar solvent may be a polar material having a sum of dP and dH in a Hansen Solubility Parameter (HSP) of 10 or greater. In an embodiment, the polar solvent PS may be ethanol or water.

In the method for manufacturing a light emitting element according to an embodiment, the method may further include providing heat to remove the non-polar organic solvent SV and the polar solvent PS after the providing of the polar solvent PS on the preliminary emission layer P-EL. For example, providing heat of 100° C. or higher may lead to removing the non-polar organic solvent SV and the polar solvent PS included in the preliminary emission layer P-EL.

Figure 11:
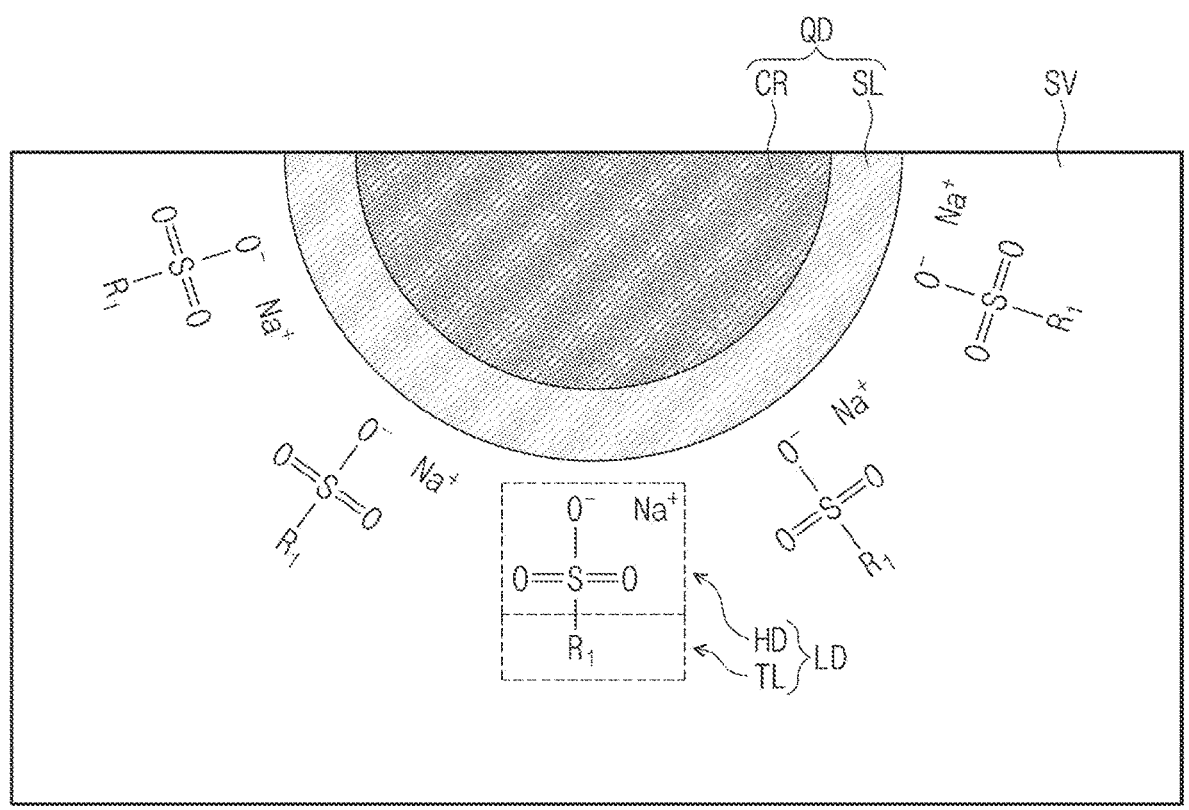
FIG. 11 is a schematic view showing a quantum dot composition according to an embodiment.

FIG. 11 is a view schematically showing a quantum dot composition according to an embodiment. FIG. 11 illustrates, as an example, a quantum dot QD provided in a preliminary emission layer P-EL and a ligand LD bonded to a quantum dot surface. FIG. 11 illustrates an example in which the ligand LD bonded to the surface of the quantum dot has a structure represented by Formula 1. In FIG. 11, $R_1$ may be a substituted or unsubstituted alkyl group having 7 to 30 carbon atoms, or a substituted or unsubstituted aryl group having 6 to 30 ring-forming carbon atoms.

As shown in FIG. 11, the quantum dot QD includes a core CR and a shell SL, and a head portion HD of the ligand LD may include an ion bond material, or a material having strong polarity, which is a polar solvent dissociative functional group, such as an oxy group and an amine group. In a non-polar organic solvent SV, the head portion HD may maintain the bonding to the shell SL surface of the quantum dot QD through coordination bonding, hydrogen bonding, ionic bonding, van der Waals bonding, etc. For example, the head portion HD having greater polarity in the non-polar organic solvent SV may be present in a state of being bonded to the surface of the quantum dot QD, and the tail portion TL having greater non-polarity may be present in a state of being exposed to the outside of the quantum dot QD to be adjacent to the non-polar organic solvent SV.

Referring to FIGS. 10 and 11 together, when the polar solvent PS is applied to the preliminary emission layer P-EL formed through the quantum dot composition, the head portion HD bonded to the surface of the quantum dot QD may be dissociated through the polar solvent PS, thereby allowing the ligand LD to be dissociated from the quantum dot QD. Accordingly, the ligand LD is not bonded to the surface of the quantum dot QD included in the emission layer EL (see FIG. 5), and thus the quantum dot QD may stay in the surface-modified state in which no other material is bonded to the surface thereof in the emission layer EL.

In the quantum dot according to an embodiment, an organic ligand is bonded in the quantum dot composition used to deliver the quantum dots, thereby ensuring dispersibility in a non-polar solvent, and when applied to an emission layer of a light emitting element, the organic ligand is then dissociated through a polar solvent to prevent or reduce other material from being bonded to the surface of the quantum dot, thereby alleviating charge injection interference caused by the ligand. For example, the light emitting element including the quantum dot according to an embodiment may have improved charge transfer properties. The ligand residues RS (FIG. 5) generated by the dissociation of the ligand LD from the quantum dot QD may be removed after the providing of a polar solvent to form an emission layer (S200). For example, in the providing of a polar solvent to form an emission layer (S200), the ligand residues may be washed away by the polar solvent, or thereafter, the cleaning of the ligand residues may be additionally performed. The ligand residues RS (FIG. 5) are mostly removed in the cleaning, but some may remain in the emission layer EL (FIG. 5).

Hereinafter, the present disclosure will be described in more detail via Examples and Comparative Examples. The Examples below are only presented as examples to help the understanding of the present disclosure, and thus the scope of the present disclosure is not limited thereto.

1. Preparation of Quantum Dot Composition

Quantum dot composites including the ligand structure of Compounds 1 to 23 bonded to surfaces of quantum dots, and quantum dot composites including the ligand structure of Comparative Example Compounds C1, C2, and C3 bonded to surfaces of quantum dots were each dispersed in an organic solvent to prepare quantum dot composition inks. Octane was used as the organic solvent, and the quantum dot composition inks of the Examples and Comparative Examples were prepared by dispersing the quantum dot composites of the Examples and Comparative Examples in octane in an amount of about 1 wt %. In the quantum dot composites, the ligand structure respectively bonded to the quantum dot surface in each Example and Comparative Example is as follows:

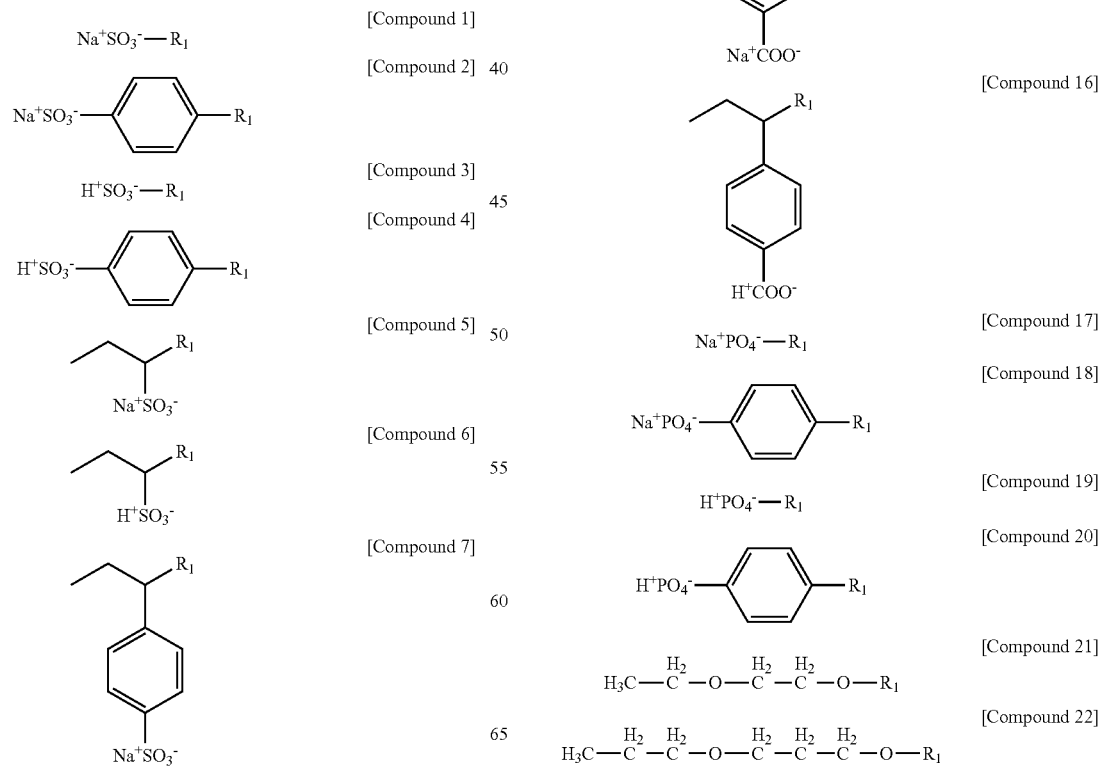

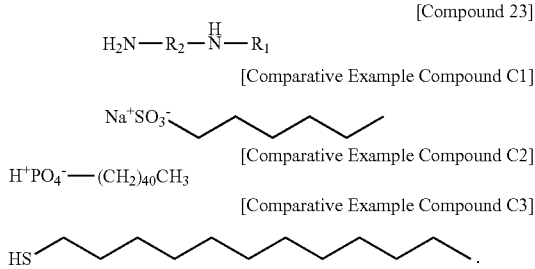

In Compounds 1 to 23, $R_1$ is a substituted or unsubstituted alkyl group having 7 to 30 carbon atoms, or a substituted or unsubstituted aryl group having 6 to 30 ring-forming carbon atoms.

[Dispersion Particle Size Measurement]

Dispersion particle sizes of the quantum dot compositions of Examples 1 to 23 (including the ligands with the structures of Compounds 1 to 23 according to an embodiment of the present disclosure), and the quantum dot compositions of Comparative Examples 1 to 3 (including the ligands with the structures of Comparative Example Compounds C1 and C3), were all measured using a ELSZ-2000ZS (Otsuka), and the results are shown in Table 1.

TABLE 1

| Quantum dot composition | Dispersion particle size (nm) | Dispersion particle size after 30 days (nm) |
|---|---|---|
| Example 1 | 8 | 8 |
| Example 2 | 8 | 8 |
| Example 3 | 7 | 7 |
| Example 4 | 8 | 8 |
| Example 5 | 8 | 8 |
| Example 6 | 7 | 7 |
| Example 7 | 9 | 9 |
| Example 8 | 9 | 9 |
| Example 9 | 7 | 7 |
| Example 10 | 7 | 7 |
| Example 11 | 7 | 7 |
| Example 12 | 8 | 8 |
| Example 13 | 7 | 7 |
| Example 14 | 8 | 8 |
| Example 15 | 7 | 7 |
| Example 16 | 9 | 9 |
| Example 17 | 9 | 9 |
| Example 18 | 7 | 7 |
| Example 19 | 7 | 7 |
| Example 20 | 7 | 7 |
| Example 21 | 8 | 8 |
| Example 22 | 7 | 7 |
| Example 23 | 8 | 8 |
| Comparative Example 1 | 60 | 188 |
| Comparative Example 2 | 7 | 8 |
| Comparative Example 3 | 7 | 8 |

Referring to Table 1, unlike the quantum dot compositions of the Examples, the quantum dot composition of Comparative Example 1 included a ligand containing an alkyl group having 6 carbon atoms (e.g., fewer than 7) bonded to a quantum dot, such that dispersibility in octane (a non-polar solvent) was reduced and dispersion particle size was significantly increased.

[Discharge Stability Measurement]

The inkjet head discharge stability of each of the quantum dot compositions of Examples 1 to 23 and the quantum dot compositions of Comparative Examples 1 to 3 was evaluated, and the results are shown in Table 2. The discharge stability was evaluated in terms of the attachment accuracy, and for 30 days of discharge, an attachment accuracy of ±5 μm in the x- and y-axis directions was evaluated as spec.-in (e.g., within specifications).

TABLE 2

| Quantum dot composition | Discharge stability for 30 days |
|---|---|
| Example 1 | Spec.-in |
| Example 2 | Spec.-in |
| Example 3 | Spec.-in |
| Example 4 | Spec.-in |
| Example 5 | Spec.-in |
| Example 6 | Spec.-in |
| Example 7 | Spec.-in |
| Example 8 | Spec.-in |
| Example 9 | Spec.-in |
| Example 10 | Spec.-in |
| Example 11 | Spec.-in |
| Example 12 | Spec.-in |
| Example 13 | Spec.-in |
| Example 14 | Spec.-in |
| Example 15 | Spec.-in |
| Example 16 | Spec.-in |
| Example 17 | Spec.-in |
| Example 18 | Spec.-in |
| Example 19 | Spec.-in |
| Example 20 | Spec.-in |
| Example 21 | Spec.-in |
| Example 22 | Spec.-in |
| Example 23 | Spec.-in |
| Comparative Example 1 | N.G. |
| Comparative Example 2 | Spec.-in |
| Comparative Example 3 | Spec.-in |

Referring to Table 2, it is seen that the quantum dot composition of Comparative Example 1 had inferior dispersibility in the non-polar solvent, compared to the quantum dot compositions of the Examples, thereby being evaluated as fail (e.g., N.G. or outside of specifications) with respect to discharge stability.

[Evaluation of Light Emitting Element Property]

A ITO glass substrate (25×25 mm, 15 Ω/sq) as an OLED glass (Samsung Corning), was ultrasonically washed using distilled water and isopropanol, and UV/ozone-cleaned for 30 minutes. PEDOT-PSS (Clevios AI4083) was spin coated on the cleaned substrate, and baking at 110° C. for 30 minutes was performed to form a hole injection layer having a thickness of about 40 nm. A 1.1 wt % polyvinyl carbazole solution in chlorobenzene was prepared, and the solution was spin coated on the hole injection layer, and then, baking at 150° C. for 30 minutes in a glove box under a nitrogen atmosphere was performed to form a hole transport layer having a thickness of about 30 nm. An emission layer having a thickness of about 35 nm was formed by spin coating a corresponding one of the quantum dot compositions of the Examples or Comparative Examples on the hole transport layer. Subsequently, a solution of 2.0 wt % ZnO nanoparticles dispersed in ethanol (a polar solvent), was prepared, and the solution was spin coated on the emission layer, and then baking at 110° C. for 30 minutes in a glove box under a nitrogen atmosphere was performed to form an electron transport layer having a thickness of about 60 nm. On the electron transport layer, aluminum (Al) was deposited to a thickness of about 100 nm through thermal evaporation to form a cathode. Accordingly, a red quantum dot organic light emitting element was manufactured. The equipment used for the deposition was a Suicel plus 200 evaporator from Sunic System.

The driving voltage, efficiency, and color purity of each of the quantum dot light emitting elements manufactured in the element preparation example were measured, and the results are shown in Table 3. The color coordinates were measured with power supplied from a current-voltmeter (Keithley SMU 236), using a luminance meter PR650. Luminance was measured with power supplied from a current-voltmeter (Keithley SMU 236), using a luminance meter PR650. The luminous efficiency was measured with power supplied from a current-voltmeter (Keithley SMU 236), using a luminance meter PR650.

TABLE 3

| Light emitting element | Emission layer forming composition | Driving voltage (V) | Efficiency (cd/A) | Color coordinate | |
|---|---|---|---|---|---|
| | | | | CIEx | CIEy |
| Example element 1 | Example 1 | 3.2 | 7.2 | 0.69 | 0.31 |
| Example element 2 | Example 2 | 3.4 | 7.4 | 0.69 | 0.31 |
| Example element 3 | Example 3 | 3.3 | 7.0 | 0.69 | 0.31 |
| Example element 4 | Example 4 | 3.3 | 7.4 | 0.69 | 0.31 |
| Example element 5 | Example 5 | 3.2 | 7.0 | 0.69 | 0.30 |
| Example element 6 | Example 6 | 3.3 | 7.2 | 0.69 | 0.31 |
| Example element 7 | Example 7 | 3.3 | 7.3 | 0.69 | 0.30 |
| Example element 8 | Example 8 | 3.2 | 6.9 | 0.69 | 0.31 |
| Example element 9 | Example 9 | 3.4 | 7.2 | 0.69 | 0.31 |
| Example element 10 | Example 10 | 3.3 | 7.1 | 0.69 | 0.31 |
| Example element 11 | Example 11 | 3.2 | 7.2 | 0.69 | 0.30 |
| Example element 12 | Example 12 | 3.4 | 7.5 | 0.69 | 0.30 |
| Example element 13 | Example 13 | 3.3 | 7.3 | 0.69 | 0.30 |
| Example element 14 | Example 14 | 3.3 | 7.8 | 0.69 | 0.31 |
| Example element 15 | Example 15 | 3.2 | 7.2 | 0.69 | 0.30 |
| Example element 16 | Example 16 | 3.3 | 7.4 | 0.69 | 0.31 |
| Example element 17 | Example 17 | 3.3 | 7.3 | 0.69 | 0.30 |
| Example element 18 | Example 18 | 3.2 | 7.1 | 0.69 | 0.31 |
| Example element 19 | Example 19 | 3.4 | 7.3 | 0.69 | 0.31 |
| Example element 20 | Example 20 | 3.3 | 7.4 | 0.69 | 0.31 |
| Example element 21 | Example 21 | 3.2 | 7.5 | 0.69 | 0.30 |
| Example element 22 | Example 22 | 3.4 | 7.5 | 0.69 | 0.30 |
| Example element 23 | Example 23 | 3.3 | 7.3 | 0.69 | 0.30 |
| Comparative Example element 1 | Comparative Example 1 | 3.3 | 7.2 | 0.69 | 0.31 |
| Comparative Example element 2 | Comparative Example 2 | 4.8 | 5.4 | 0.69 | 0.30 |
| Comparative Example element 3 | Comparative Example 3 | 5.0 | 5.5 | 0.69 | 0.31 |

Referring to the results of Table 3, Comparative Example element 2 having the quantum dot composition of Comparative Example 2 as an emission layer forming composition, includes an alkyl group having 41 carbon atoms (e.g., more than 30) as a ligand, which prevents or reduces ligand dissociation from the quantum dot even when a polar solvent is added for forming an electron transport layer, and thus it is confirmed that when applied to the element, the driving voltage increases and the luminous efficiency decreases. Comparative Example element 3 having the quantum dot composition of Comparative Example 3 as an emission layer forming composition, includes a thiol group head portion having a slightly lower polarity than the Example quantum dot composition ligands, which prevents or reduces ligand dissociation from the quantum dot even when a polar solvent is added for forming an electron transport layer, and thus it is confirmed that when applied to the element, the driving voltage increases and the luminous efficiency decreases. In comparison, the light emitting element of an embodiment forms an emission layer from the quantum dot composition including the ligand structure according to an embodiment of the present disclosure to readily disperse the quantum dot-ligand composite in a non-polar solvent when the emission layer forming composition is discharged through an inkjet method, thereby increasing discharge stability, while dissociating and washing away the ligand from the quantum dot through the polar solvent when applied to the emission layer, thereby reducing the driving voltage and increasing the luminous efficiency of the light emitting element.

Figure 12:
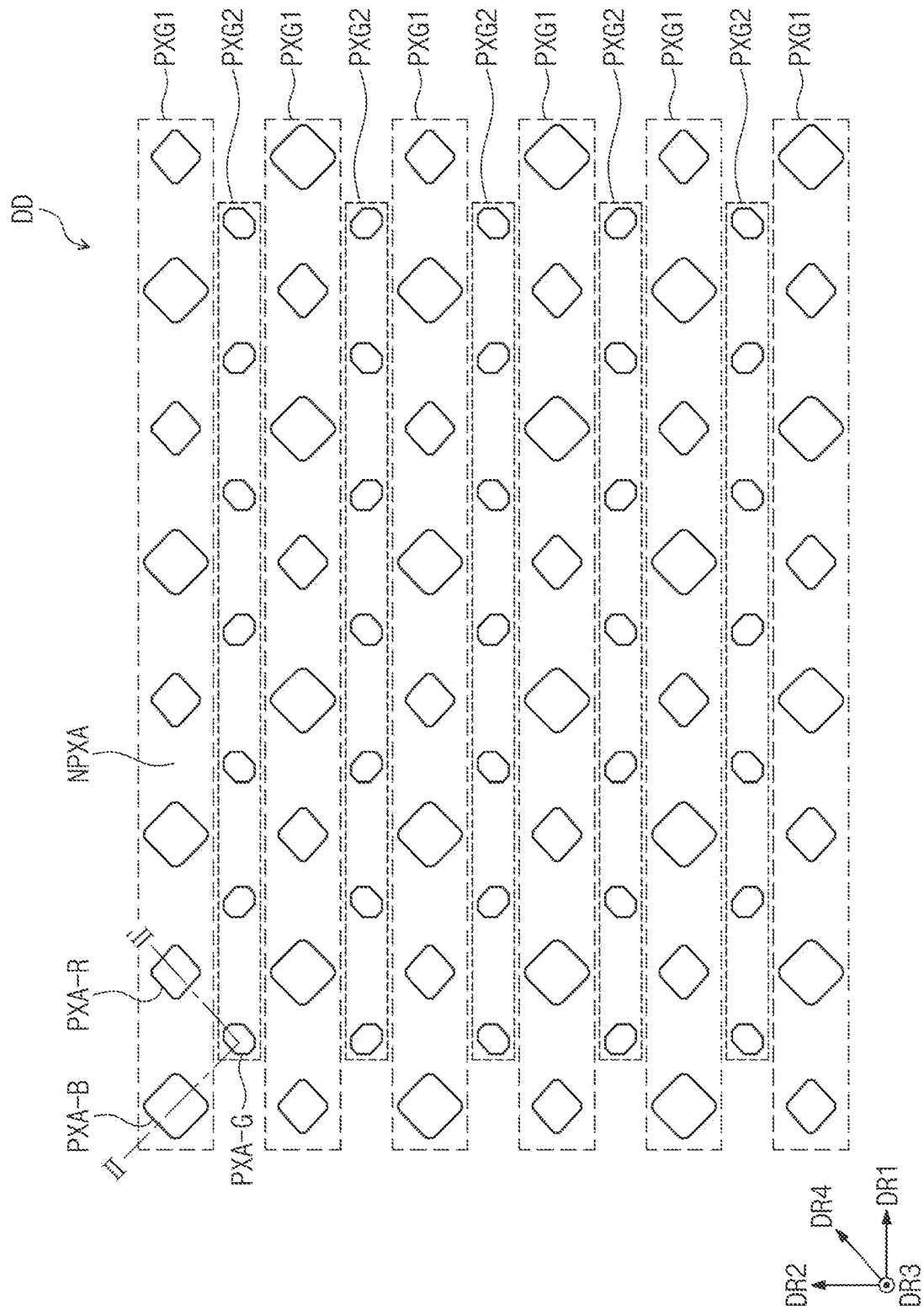
FIG. 12 is a plan view showing a display device pixel layout according to an embodiment.

FIG. 12 is a plan view of a display device DD pixel layout according to an embodiment. FIG. 13 is a cross-sectional view of a display device DD according to an embodiment. FIG. 13 is a cross-sectional view corresponding to line II-II' of FIG. 12.

Referring to FIGS. 12 and 13, the display device DD of an embodiment may include a plurality of light emitting elements ED-1, ED-2, and ED-3, and the light emitting elements ED-1, ED-2, and ED-3 may include emission layers EL-B, EL-G, and EL-R having quantum dots QD1, QD2, and QD3.

In addition, the display device DD of an embodiment may include a display panel DP containing the plurality of light emitting elements ED-1, ED-2 and ED-3, and a light control layer PP disposed on the display panel DP. In some embodiments, in contrast to the view illustrated in the drawing, the light control layer PP may be omitted from the display device DD of an embodiment.

The display panel DP may include a base substrate BS, a circuit layer DP-CL, and a display element layer DP-EL provided on the base substrate BS, and the display element layer DP-EL may include a pixel defining film PDL, light emitting elements ED-1, ED-2 and ED-3 defined by (e.g., disposed between inner-walls of) the pixel defining film PDL, and an encapsulation layer TFE disposed on the light emitting elements ED-1, ED-2 and ED-3.

The display device DD may include a non-light emission area NPXA and light emission areas PXA-B, PXA-G and PXA-R. Each of the light emission areas PXA-B, PXA-G and PXA-R may be an area (region) to emit light generated from each of the light emitting elements ED-1, ED-2 and ED-3. The light emission areas PXA-B, PXA-G and PXA-R may be spaced apart from one another on (in) a plane.

The light emission areas PXA-B, PXA-G and PXA-R may be divided into a plurality of groups according to the color of light generated from the light emitting elements ED-1, ED-2, and ED-3. In the example display device DD of an embodiment illustrated in FIGS. 12 and 13, three light emission areas PXA-B, PXA-G, and PXA-R to emit blue light, green light, and red light, respectively, are illustrated. For example, the display device DD of an embodiment may include a blue light emission area PXA-B, a green light emission area PXA-G, and a red light emission area PXA-R, which are separated from one another.

The plurality of light emitting elements ED-1, ED-2, and ED-3 may be to emit light in different wavelength regions. For example, in an embodiment, the display device DD may include a first light emitting element ED-1 to emit blue light, a second light emitting element ED-2 to emit green light, and a third light emitting element ED-3 to emit red light. However, embodiments of the present disclosure are not limited thereto, and the first to third light emitting elements ED-1, ED-2, and ED-3 may be to emit light in the same wavelength region or to emit light in at least one different wavelength region.

For example, the blue light emission area PXA-B, the green light emission area PXA-G, and the red light emission area PXA-R of the display device DD may correspond to the first light emitting element ED-1, the second light emitting element ED-2, and the third light emitting element ED-3, respectively.

The second emission layer EL-G of the second light emitting element ED-2, and the third emission layer EL-R of the third light emitting element ED-3 may include a second quantum dot QD2 and a third quantum dot QD3, respectively. The second quantum dot QD2 and the third quantum dot QD3 may be to emit green light as the second light, and red light as the third light, respectively.

Each of the first to third quantum dots QD1, QD2, and QD3 may have no other materials bonded to the surfaces (outer surfaces) thereof. For each of the first to third quantum dots QD1, QD2, and QD3, the description of the quantum dot QD in which the ligand bonded to the surface thereof is removed by a polar solvent, as described above in the light emitting element of an embodiment, may be suitably applied.

Each of the first to third emission layers EL-B, EL-G, and EL-R including each of the first to third quantum dots QD1, QD2, and QD3 may be derived from a quantum dot composition including a ligand bonded to a surface of a quantum dot. Each of the first to third emission layers EL-B, EL-G, and EL-R may include the first to third quantum dots QD1, QD2, and QD3 formed when a ligand having a head portion bonded to the quantum dot surface and containing a polar solvent dissociative functional group, and a tail portion connected to the head portion is dissociated from the quantum dot surface.

In addition, each of the first to third emission layers EL-B, EL-G, and EL-R may further include residues (reaction residues) derived from the ligand as dissociated in the polar solvent. The reaction residues may include a polar solvent dissociative functional group contained in the head portion of the ligand, and the non-polar tail portion to ensure dispersibility in a non-polar organic solvent.

In an embodiment, the first to third quantum dots QD1, QD2, and QD3 included in the light emitting elements ED-1, ED-2, and ED-3 may be formed of different core materials. In some embodiments, the first to third quantum dots QD1, QD2, and QD3 may be formed of the same core material, or two quantum dots selected from the first to third quantum dots QD1, QD2, and QD3 may be formed of the same core material, and the rest may be formed of different core materials.

In an embodiment, the first to third quantum dots QD1, QD2, and QD3 may have different diameters. For example, the first quantum dot QD1 used in the first light emitting element ED-1 emitting light in a relatively short wavelength range may have a relatively smaller average diameter than the second quantum dot QD2 of the second light emitting element ED-2 and the third quantum dot QD3 of the third light emitting element ED-3, each emitting light in a relatively long wavelength region. In the present description, the term "average diameter" refers to the arithmetic mean of the diameters of a plurality of quantum dot particles. In some embodiments, the diameter of the quantum dot particle may be the average value of the cross-sectional width of the quantum dot particle.

In the display device DD of an embodiment, as shown in FIGS. 12 and 13, the areas of the light emission areas PXA-B, PXA-G, and PXA-R may each be different from one another. In this case, the term "area" may refer to an area as viewed on a plane defined by the first direction DR1 and the second direction DR2.

The light emission areas PXA-B, PXA-G, and PXA-R may have different areas (e.g., pixel areas) according to the color to be emitted from the emission layers EL-B, EL-G and EL-R of the light emitting elements ED-1, ED-2 and ED-3. For example, referring to FIGS. 12 and 13, the blue light emission area PXA-B corresponding to the first light emitting element ED-1 to emit blue light may have the largest area, and the green light emission area PXA-G corresponding to the second light emitting element ED-2 to emit green light may have the smallest area in the display device DD of an embodiment. However, embodiments of the present disclosure are not limited thereto, and the light emission areas PXA-B, PXA-G, and PXA-R may be to emit light other than blue light, green light, and red light, or the light emission areas PXA-B, PXA-G, and PXA-R may have the same area, or the light emission areas PXA-B, PXA-G, and PXA-R may be provided at different area ratios (e.g., relative areas) from those shown in FIG. 12.

Each of the light emission areas PXA-B, PXA-G, and PXA-R may be an area separated (and defined) by a pixel defining film PDL. The non-light emission areas NPXA may be areas between neighboring light emission areas PXA-B, PXA-G, and PXA-R, and may correspond to the pixel defining film PDL. In the present description, each of the light emission areas PXA-B, PXA-G, and PXA-R may correspond to a pixel. The pixel defining film PDL may separate the light emitting elements ED-1, ED-2, and ED-3. The emission layers EL-B, EL-G, and EL-R of the light emitting elements ED-1, ED-2, and ED-3 may each be disposed and separated in an opening OH defined by the pixel defining film PDL.

The pixel defining film PDL may be formed of a polymer resin. For example, the pixel defining film PDL may be formed including a polyacrylate-based resin or a polyimide-based resin. In addition, the pixel defining film PDL may be formed by further including an inorganic material in addition to the polymer resin. The pixel defining film PDL may be formed to include a light absorbing material, or may be formed to include a black pigment and/or a black dye. The pixel defining film PDL formed to include a black pigment and/or a black dye may implement a black pixel defining film. When forming the pixel defining film PDL, carbon black may be used as the black pigment and/or the black dye, but embodiments of the present disclosure are not limited thereto.

In some embodiments, the pixel defining film PDL may be formed of an inorganic material. For example, the pixel defining film PDL may be formed to include silicon nitride (SiNx), silicon oxide (SiOx), silicon oxide (SiOxNy), etc. The pixel defining film PDL may define the light emission areas PXA-B, PXA-G, and PXA-R. The light emission areas PXA-B, PXA-G, and PXA-R, and the non-light emission area NPXA may be separated by the pixel defining film PDL.

Each of the light emitting elements ED-1, ED-2, and ED-3 may include a first electrode EL1, a hole transport region HTR, emission layers EL-B, EL-G, and EL-R, an electron transport region ETR, and a second electrode EL2. The description in FIG. 4 may be applied to the first electrode EL1, the hole transport region HTR, the electron transport region ETR, and the second electrode EL2, except that the first to third quantum dots QD1, QD2, and QD3 included in the emission layers EL-B, EL-G, and EL-R are different from one another in the light emitting elements ED-1, ED-2, and ED-3 included in the display device DD of an embodiment.

An encapsulation layer TFE may cover the light emitting elements ED-1, ED-2, and ED-3. The encapsulation layer TFE may be a single layer or a laminated layer (stack) of a plurality of layers. The encapsulation layer TFE may be a thin film encapsulation layer. The encapsulation layer TFE may protect the light emitting elements ED-1, ED-2, and ED-3. The encapsulation layer TFE may cover an upper surface of the second electrode EL2 disposed in the opening OH, and may fill the opening OH.

In FIG. 13, the hole transport region HTR and the electron transport region ETR are illustrated as providing a common layer while covering the pixel defining film PDL, but embodiments of the present disclosure are not limited thereto. In an embodiment, the hole transport region HTR and the electron transport region ETR may be disposed (e.g., only disposed) in the opening OH defined by the pixel defining film PDL.

For example, when the hole transport region HTR and the electron transport region ETR in addition to the emission layers EL-B, EL-G, and EL-R are provided through an inkjet printing method, the hole transport region HTR, the emission layers EL-B, EL-G, and EL-R, the electron transport region ETR, etc. may be provided to correspond to the defined opening OH between the pixel defining film PDL. However, embodiments are not limited thereto, and as shown in FIG. 13, the hole transport region HTR and the electron transport region ETR may cover the pixel defining film PDL without being patterned, and be provided as one common layer regardless of a method of providing each functional layer.

In the display device DD of an embodiment illustrated in FIG. 13, although the thicknesses of the emission layers EL-B, EL-G, and EL-R of the first to third light emitting elements ED-1, ED-2, and ED-3 are illustrated as being similar to one another, embodiments are not limited thereto. For example, in an embodiment, the thicknesses of the emission layers EL-B, EL-G, and EL-R of the first to third light emitting elements ED-1, ED-2, and ED-3 may be different from one another.

Referring to FIG. 12, the blue light emission areas PXA-B and the red light emission areas PXA-R may be alternatingly arranged in the first direction DR1 to form a first group PXG1. The green light emission areas PXA-G may be arranged in the first direction DR1 to form a second group PXG2.

The first group PXG1 and the second group PXG2 may be spaced apart in the second direction DR2. Each of the first group PXG1 and the second group PXG2 may be provided in plural. The first groups PXG1 and the second groups PXG2 may be alternatingly arranged in the second direction DR2.

One green light emission area PXA-G may be disposed spaced apart from one blue light emission area PXA-B or one red light emission area PXA-R in the fourth direction DR4. The fourth direction DR4 may be a direction between the first direction DR1 and the second direction DR2.

The arrangement structure of the light emission areas PXA-B, PXA-G and PXA-R shown in FIG. 12 may have a PENTILE® (Samsung Display Co., Ltd.) structure, for example a RGBG matrix structure or diamond shape arrangement. However, the arrangement structure of the light emission areas PXA-B, PXA-G, and PXA-R in the display device DD according to an embodiment is not limited to the arrangement structure shown in FIG. 12. For example, in an embodiment, the light emission areas PXA-B, PXA-G, and PXA-R may have a stripe structure in which the blue light emission area PXA-B, the green light emission area PXA-G, and the red light emission area PXA-R may be alternatingly arranged along the first direction DR1.

Referring to FIG. 3 and FIG. 13, the display device DD of an embodiment further includes a light control layer PP. The light control layer PP may block or reduce external light incident to the display panel DP from the outside the display device DD. The light control layer PP may block or reduce at least a portion of the external light. For example. the light control layer PP may minimize or reduce a reflection due to external light.

In an embodiment illustrated in FIG. 13, the light control layer PP may include a color filter layer CFL. For example, the display device DD of an embodiment may further include the color filter layer CFL disposed on the light emitting elements ED-1, ED-2, and ED-3 of the display panel DP.

In the display device DD of an embodiment, the light control layer PP may include a base layer BL and a color filter layer CFL.

The base layer BL may be a member providing a base surface on which the color filter layer CFL is disposed. The base layer BL may be a glass substrate, a metal substrate, a plastic substrate, etc. However, embodiments of the present disclosure are not limited thereto, and the base layer BL may be an inorganic layer, an organic layer, or a composite material layer.

The color filter layer CFL may include a light blocking unit BM and a color filter CF. The color filter may include a plurality of filters CF-B, CF-G, and CF-R. For example, the color filter layer CFL may include a first filter CF-B transmitting a first color light, a second filter CF-G transmitting a second color light, and a third filter CF-R transmitting a third color light. For example, the first filter CF-B may be a blue filter, the second filter CF-G may be a green filter, and the third filter CF-R may be a red filter.

Each of the filters CF-B, CF-G, and CF-R may include a polymer photosensitive resin and a pigment or a dye. The first filter CF-B may include a blue pigment or a blue dye, the second filter CF-G may include a green pigment or a green dye, and the third filter CF-R may include a red pigment or a red dye.

In some embodiments, the first filter CF-B may not include a pigment or a dye. The first filter CF-B may include a polymer photosensitive resin, but not include a pigment or a dye. The first filter CF-B may be transparent. The first filter CF-B may be formed of a transparent photosensitive resin.

The light blocking unit BM may be a black matrix. The light blocking unit BM may be formed to include an organic light blocking material or an inorganic light blocking material, both including a black pigment or a black dye. The light blocking unit BM may prevent or reduce light leakage, and separate boundaries between the adjacent filters CF-B, CF-G, and CF-R.

The color filter layer CFL may further include a buffer layer BFL. For example, the buffer layer BFL may be a protection layer to protect the filters CF-B, CF-G, and CF-R. The buffer layer BFL may be an inorganic material layer including at least one inorganic material among silicon nitride, silicon oxide, and silicon oxynitride. The buffer layer BFL may be formed of a single layer or a plurality of layers.

In an embodiment shown in FIG. 13, the first filter CF-B of the color filter layer CFL is illustrated to overlap the second filter CF-G and the third filter CF-R, but embodiments of the present disclosure are not limited thereto. For example, the first to third filters CF-B, CF-G, and CF-R may be separated by the light blocking unit BM and may not overlap one another. In an embodiment, each of the first to third filters CF-B, CF-G, and CF-R may be disposed correspondingly to each of the blue light emission area PXA-B, green light emission area PXA-G, and red light emission area PXA-R.

In contrast to FIG. 13 and/or the like, the display device DD of an embodiment may include a polarizing layer as a light control layer PP instead of the color filter layer CFL. The polarizing layer may block or reduce external light provided to the display panel DP from the outside. The polarizing layer may block or reduce a part of external light.

In some embodiments, the polarizing layer may reduce reflected light generated in the display panel DP by external light. For example, the polarizing layer may block or reduce reflected light when light provided from outside the display device DD is incident to the display panel DP and exits again. The polarizing layer may be a circular polarizer to prevent or reduce such reflection, or the polarizing layer may include a linear polarizer and a λ/4 phase retarder. In some embodiments, the polarizing layer may be disposed on the base layer BL to be exposed or the polarizing layer may be disposed under the base layer BL.

The display device of an embodiment includes, in an emission layer, a quantum dot having a ligand removed by a polar solvent to prevent or reduce other materials from being bonded to the surface thereof, thereby improving charge injection properties inhibited by the ligand and exhibiting excellent luminous efficiency. For example, the quantum dot provided in the display device of an embodiment is provided as a quantum dot composition having the ligand bonded to a quantum dot and having excellent dispersibility in a non-polar solvent, which is washed away in the polar solvent when applied to the emission layer so that substantially no materials are bonded to the surface of the quantum dot, such that the quantum dot exhibits excellent luminous efficiency when applied to a light emitting element of the display device.

FIG. 14 is a cross-sectional view of a display device DD-1 of another embodiment of the present disclosure. In the description of the display device DD-1 according to an embodiment, content overlapping the one described above with reference to FIGS. 1 to 13 will not be described again, and the differences will be mainly described.

Referring to FIG. 14, the display device DD-1 of an embodiment may include a light control layer CCL disposed on a display panel DP-1. In addition, the display device DD-1 may further include a color filter layer CFL. The color filter layer CFL may be disposed between the base layer BL and the light control layer CCL.

The display panel DP-1 may be a light emitting display panel. For example, the display panel DP-1 may be an organic electroluminescence display panel or a quantum dot light emitting display panel.

The display panel DP-1 may include a base substrate BS, a circuit layer DP-CL provided on the base substrate BS, and a display element layer DP-EL1.

The display element layer DP-EL1 includes a light emitting element ED-a, and the light emitting element ED-a may include a first electrode EL1 and a second electrode EL2 facing each other, and a plurality of layers OL disposed between the first electrode EL1 and the second electrode EL2. The plurality of layers OL may include a hole transport region HTR (FIG. 4), an emission layer EL (FIG. 4), and an electron transport region ETR (FIG. 4). An encapsulation layer TFE may be disposed on the light emitting element ED-a.

In the light emitting element ED-a, the same content as the one described with reference to FIG. 4 may be applied to the first electrode EL1, the hole transport region HTR, the electron transport region ETR, and the second electrode EL2. However, in the light emitting element ED-a included in the display panel DP-1 of an embodiment, the emission layer may include a host and a dopant (which are organic electroluminescent materials) or may include the quantum dots described with reference to FIGS. 1 to 13. In the display panel DP-1 of an embodiment, the light emitting element ED-a may be to emit blue light.

The light control layer CCL may include a plurality of partition walls BK disposed spaced apart from each other and light control units CCP-B, CCP-G, and CCP-R disposed between the partition walls BK. The partition walls BK may be formed including a polymer resin and a coloring additive. The partition walls BK may be formed to include a light absorbing material, or formed to include a pigment or a dye. For example, the partition walls BK may include a black pigment and/or a black dye to implement a black partition wall. When forming the black partition wall, carbon black and/or the like may be used as the black pigment or the black dye, but embodiments of the present disclosure are not limited thereto.

The light control layer CCL may include a first light control unit CCP-B to transmit first light, a second light control unit CCP-G including a second quantum dot QD2-a to convert the first light to second light, and a third light control unit CCP-R including a third quantum dot QD3-a to convert the first light to third light. The second light may be light of a longer wavelength region than the first light, and the third light may be light of a longer wavelength region than the first light and the second light. For example, the first light may be blue light, the second light may be green light, and the third light may be red light. Regarding the quantum dots QD2-a and QD3-a included in the light control units CCP-B, CCP-G, and CCP-R, the same content as the one for the quantum dots QD2 and QD3 used in the emission layers EL-G and EL-R illustrated in FIG. 13 may be applied.

The light control layer CCL may further include a capping layer CPL. The capping layer CPL may be disposed on the light control units CCP-B, CCP-G, and CCP-R, and the partition walls BK. The capping layer CPL may serve to prevent or reduce penetration of moisture and/or oxygen (hereinafter, referred to as "moisture/oxygen"). The capping layer may be disposed on the light control units CCP-B, CCP-G, and CCP-R to prevent or reduce the light control units CCP-B, CCP-G, and CCP-R from being exposed to moisture/oxygen. The capping layer CPL may include at least one inorganic layer.

The display device DD-1 of an embodiment may include a color filter layer CFL disposed on the light control layer CCL, and the descriptions of FIG. 13 may be applied to the color filter layer CFL and the base layer BL.

The display device DD-1 of an embodiment may exhibit excellent color reproducibility by including, in the light control layer CCL, the quantum dots QD2-*a* and QD3-*a* in which a ligand bonded to the surface thereof is removed.

In addition, in the display device DD-1 of an embodiment, the light emitting element ED-a of the display panel DP-1 may include an emission layer containing a quantum dot in which a ligand is removed, and in this case, the display panel DP-1 may exhibit excellent luminous efficiency A quantum dot composition of an embodiment may be used as an emission layer material capable of exhibiting improved luminous efficiency by preventing or reducing degradation of charge injection properties even when applied to the emission layer, since a ligand bonded to a surface of a quantum dot may be dissociated through a polar solvent.

A light emitting element and a display device of an embodiment may exhibit improved luminous efficiency by including a quantum dot not having degradation of charge injection properties in an emission layer.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the present disclosure has been described with reference to example embodiments of the present disclosure, it will be understood that the present disclosure should not be limited to these example embodiments but various changes and modifications can be made by those skilled in the art without departing from the spirit and scope of the present disclosure.

Accordingly, the technical scope of the present disclosure is not intended to be limited to the contents set forth in the detailed description of the specification, but is intended to be defined by the appended claims and equivalents thereof.

What is claimed is:

1. A method of manufacturing a light emitting element, the method comprising:
    forming a first electrode;
    forming a hole transport region on the first electrode;
    providing, on the hole transport region, a quantum dot composition containing a quantum dot composite having a quantum dot and a ligand bonded to a surface of the quantum dot to form a preliminary emission layer;
    providing a polar solvent on the preliminary emission layer to form an emission layer, wherein in the providing of the polar solvent on the preliminary emission layer, the ligand is dissociated from the quantum dot in the polar solvent;
    forming an electron transport region on the emission layer; and
    forming a second electrode on the electron transport region.

2. A method of manufacturing a light emitting element, the method comprising:
    forming a first electrode;
    forming a hole transport region on the first electrode;
    providing, on the hole transport region, a quantum dot composition containing a quantum dot composite having a quantum dot and a ligand bonded to a surface of the quantum dot to form a preliminary emission layer:
    providing a polar solvent on the preliminary emission layer to form an emission layer;
    forming an electron transport region on the emission layer; and
    forming a second electrode on the electron transport region,
    wherein the ligand comprises a head portion bonded to the surface of the quantum dot and containing a polar solvent dissociative functional group, and a tail portion connected to the head portion.

3. A method of manufacturing a light emitting element, the method comprising:
    forming a first electrode;
    forming a hole transport region on the first electrode;
    providing, on the hole transport region, a quantum dot composition containing a quantum dot composite having a quantum dot and a ligand bonded to a surface of the quantum dot to form a preliminary emission layer;
    providing a polar solvent on the preliminary emission layer to form an emission layer;
    forming an electron transport region on the emission layer; and
    forming a second electrode on the electron transport region,
    wherein the providing of the polar solvent on the preliminary emission layer and the forming of the electron transport region on the emission layer are performed in a single process.

4. The method of claim 3, wherein the providing of the polar solvent on the preliminary emission layer and the forming of the electron transport region on the emission layer comprise applying, on the light emitting layer, a solution in which an electron transport material is dispersed in the polar solvent.

5. The method of claim 3, wherein in the providing of the polar solvent on the preliminary emission layer, the ligand is dissociated from the quantum dot in the polar solvent.

* * * * *

UNITED STATES PATENT AND TRADEMARK OFFICE
CERTIFICATE OF CORRECTION

PATENT NO. : 12,258,504 B2
APPLICATION NO. : 18/407326
DATED : March 25, 2025
INVENTOR(S) : Changhee Lee et al.

Page 1 of 1

It is certified that error appears in the above-identified patent and that said Letters Patent is hereby corrected as shown below:

In the Claims

In Column 32, Line 33, in Claim 2, delete "layer:" and insert -- layer; --.

Signed and Sealed this
Eighth Day of July, 2025

Coke Morgan Stewart
*Acting Director of the United States Patent and Trademark Office*